(12) United States Patent
Endo et al.

(10) Patent No.: US 9,808,213 B2
(45) Date of Patent: Nov. 7, 2017

(54) IMAGE PROCESSING APPARATUS, IMAGE PROCESSING METHOD, MEDICAL IMAGE DIAGNOSTIC SYSTEM, AND STORAGE MEDIUM

(71) Applicant: CANON KABUSHIKI KAISHA, Tokyo (JP)

(72) Inventors: Takaaki Endo, Urayasu (JP); Kiyohide Satoh, Kawasaki (JP); Ryo Ishikawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 77 days.

(21) Appl. No.: 14/817,481

(22) Filed: Aug. 4, 2015

(65) Prior Publication Data

US 2016/0042248 A1  Feb. 11, 2016

(30) Foreign Application Priority Data

Aug. 11, 2014 (JP) ................................. 2014-163931
Aug. 11, 2014 (JP) ................................. 2014-163932

(51) Int. Cl.
*G06K 9/00* (2006.01)
*A61B 6/00* (2006.01)
(Continued)

(52) U.S. Cl.
CPC ............. *A61B 6/466* (2013.01); *A61B 6/469* (2013.01); *A61B 6/5223* (2013.01);
(Continued)

(58) Field of Classification Search
None
See application file for complete search history.

(56) References Cited

U.S. PATENT DOCUMENTS 6,792,370 B2  9/2004 Satoh et al.
6,993,450 B2  1/2006 Takemoto et al.
(Continued)

FOREIGN PATENT DOCUMENTS

JP  2005-169070 A  6/2005
JP  2011-125568 A  6/2011

OTHER PUBLICATIONS

U.S. Appl. No. 14/801,138, filed Jul. 16, 2015, Yasufumi Takama et al.

*Primary Examiner* — Avinash Yentrapati
(74) *Attorney, Agent, or Firm* — Fitzpatrick, Cella, Harper & Scinto

(57) ABSTRACT

An image processing apparatus includes: an obtaining unit configured to obtain three-dimensional image data and positions of a plurality of feature points in the three-dimensional image data; a designation unit configured to designate a designation point indicating a portion of interest in the three-dimensional image data; a selection unit configured to select, using information determined by a position of the designation point and the positions of the plurality of feature points, a feature point from the plurality of feature points; a generation unit configured to generate, from the three-dimensional image data, a cross section image on a plane determined based on the position of the designation point and a position of the selected feature point; and a display control unit configured to cause a display unit to display the generated cross section image.

25 Claims, 10 Drawing Sheets

US 9,808,213 B2
Page 2

(51) Int. Cl.
*A61B 8/00* (2006.01)
*G06T 7/33* (2017.01)
*A61B 8/08* (2006.01)
*A61B 5/00* (2006.01)
*A61B 5/055* (2006.01)

(52) U.S. Cl.
CPC ............ *A61B 6/5247* (2013.01); *A61B 8/469* (2013.01); *A61B 8/523* (2013.01); *A61B 8/5261* (2013.01); *G06K 9/00302* (2013.01); *G06T 7/33* (2017.01); *A61B 5/0095* (2013.01); *A61B 5/055* (2013.01); *A61B 6/502* (2013.01); *A61B 8/0825* (2013.01); *A61B 8/483* (2013.01); *G06T 2207/10081* (2013.01); *G06T 2207/10088* (2013.01); *G06T 2207/30068* (2013.01)

(56) References Cited

U.S. PATENT DOCUMENTS

| | | |
|---|---|---|
| 7,092,109 B2 | 8/2006 | Satoh et al. |
| 7,123,766 B2 * | 10/2006 | Mao ..................... G06K 9/3233 345/419 |
| 7,130,754 B2 | 10/2006 | Satoh et al. |
| 7,797,030 B2 * | 9/2010 | Lahm ...................... A61B 5/06 382/128 |
| 7,848,903 B2 | 12/2010 | Aratani et al. |
| 8,102,392 B2 | 1/2012 | Yamagata et al. |
| 8,350,897 B2 | 1/2013 | Endo et al. |
| 2004/0210138 A1 * | 10/2004 | Murashita ................ A61B 8/08 600/443 |
| 2005/0033160 A1 * | 2/2005 | Yamagata ................ A61B 6/12 600/425 |
| 2007/0083099 A1 * | 4/2007 | Henderson ......... A61B 5/02007 600/407 |
| 2007/0167699 A1 * | 7/2007 | Lathuiliere ........... G06T 7/0083 600/407 |
| 2010/0034426 A1 * | 2/2010 | Takiguchi .......... G01C 21/3602 382/106 |
| 2010/0222671 A1 * | 9/2010 | Cohen .................. A61B 5/0044 600/424 |
| 2011/0150310 A1 * | 6/2011 | Endo ..................... G06T 7/0012 382/131 |
| 2011/0216958 A1 * | 9/2011 | Satoh .................... A61B 8/5261 382/131 |
| 2011/0262015 A1 * | 10/2011 | Ishikawa .............. G06K 9/6206 382/128 |
| 2012/0249549 A1 * | 10/2012 | Endo .................... A61B 8/4416 345/419 |
| 2012/0253171 A1 * | 10/2012 | Ishikawa ................. G06T 7/33 600/411 |
| 2013/0182901 A1 * | 7/2013 | Ishida ................... G06T 7/0012 382/103 |
| 2013/0195339 A1 * | 8/2013 | Endo ........................ G06K 9/46 382/131 |
| 2014/0161331 A1 * | 6/2014 | Cohen .................... G06T 5/003 382/128 |
| 2015/0070469 A1 | 3/2015 | Yoshibayashi et al. |
| 2015/0131880 A1 * | 5/2015 | Wang .................... G06T 3/0075 382/131 |
| 2016/0334964 A1 * | 11/2016 | Jeon ......................... A61B 6/03 |

* cited by examiner

IMAGE PROCESSING APPARATUS, IMAGE PROCESSING METHOD, MEDICAL IMAGE DIAGNOSTIC SYSTEM, AND STORAGE MEDIUM

BACKGROUND OF THE INVENTION

Field of the Invention

The present invention relates to an image processing apparatus which generates a cross section image from three-dimensional image data, an image processing method, a medical image diagnostic system, and a storage medium.

Description of the Related Art

In the medical field, a doctor displays the medical image obtained by imaging an object (three-dimensional image data formed from a tomographic image group representing information of the inside of the object) on a monitor, and diagnoses a lesion portion by interpreting the displayed medical image. Medical image acquisition apparatuses (to be referred to as modalities hereinafter) which obtain three-dimensional image data include a magnetic resonance imaging apparatus (to be referred to as an MRI apparatus hereinafter), a computed tomography apparatus (to be referred to as a CT apparatus hereinafter), and a three-dimensional ultrasonic imaging apparatus.

More specifically, the doctor displays, on the monitor, a cross section image in a predetermined posture, which includes a target portion (to be referred to as a portion of interest hereinafter) such as a lesion portion in three-dimensional image data. The doctor then observes and diagnoses the portion of interest on the cross section image based on appearance features (to be referred to as image features hereinafter) of the portion of interest and its peripheral portion. As a cross section image in a predetermined posture, an image on an axial plane, sagittal plane, coronal plane, or a combination of them (three cross sections) is generally used.

In addition, Japanese Patent Laid-Open No. 2005-169070 discloses a technique of generating and displaying a cross section image including a designation point from three-dimensional image data by rotating the posture of a cross section in an arbitrary direction under a constraint condition that a cross section always includes a point designated in three-dimensional image data when changing the cross section. Furthermore, Japanese Patent Laid-Open No. 2011-125568 discloses a technique of rotating a posture around a straight line passing through two selected points of interest.

According to Japanese Patent Laid-Open Nos. 2005-169070 and 2011-125568, however, a cross section image in a predetermined posture does not always include a portion of interest and image features used as references, and hence it is not always easy to observe and diagnose the portion of interest based on the image features of the portion of interest and its peripheral portion. In addition, Japanese Patent Laid-Open Nos. 2005-169070 and 2011-125568 give no consideration to a technique of generating a cross section image including a designation point indicating a portion of interest designated in three-dimensional image data and feature points indicating known image features.

The present invention provides an image processing technique capable of generating a cross section image including a designation point indicating a portion of interest in three-dimensional image data and an image feature as a reference.

In addition, the present invention provides an image processing technique capable of generating a plurality of cross section images including designation points indicating portions of interest in three-dimensional image data and feature points to be sequentially selected.

SUMMARY OF THE INVENTION

According to one aspect of the present invention, there is provided an image processing apparatus comprising: an obtaining unit configured to obtain three-dimensional image data and positions of a plurality of feature points in the three-dimensional image data; a designation unit configured to designate a designation point indicating a portion of interest in the three-dimensional image data; a selection unit configured to select, using information determined by a position of the designation point and the positions of the plurality of feature points, a feature point from the plurality of feature points; a generation unit configured to generate, from the three-dimensional image data, a cross section image on a plane determined based on the position of the designation point and a position of the selected feature point; and a display control unit configured to cause a display unit to display the generated cross section image.

According to another aspect of the present invention, there is provided an image processing method for an image processing apparatus, comprising: an obtaining step of obtaining three-dimensional image data and positions of a plurality of feature points in the three-dimensional image data; a designation step of designating a designation point indicating a portion of interest in the three-dimensional image data; a selection step of selecting, using information determined by a position of the designation point and the positions of the plurality of feature points, a feature point from the plurality of feature points; a generation step of generating, from the three-dimensional image data, a cross section image on a plane determined based on the position of the designation point and a position of the selected feature point; and a display control step of causing a display unit to display the generated cross section image.

Further features of the present invention will become apparent from the following description of exemplary embodiments (with reference to the attached drawings).

DESCRIPTION OF THE EMBODIMENTS

Figure 1:
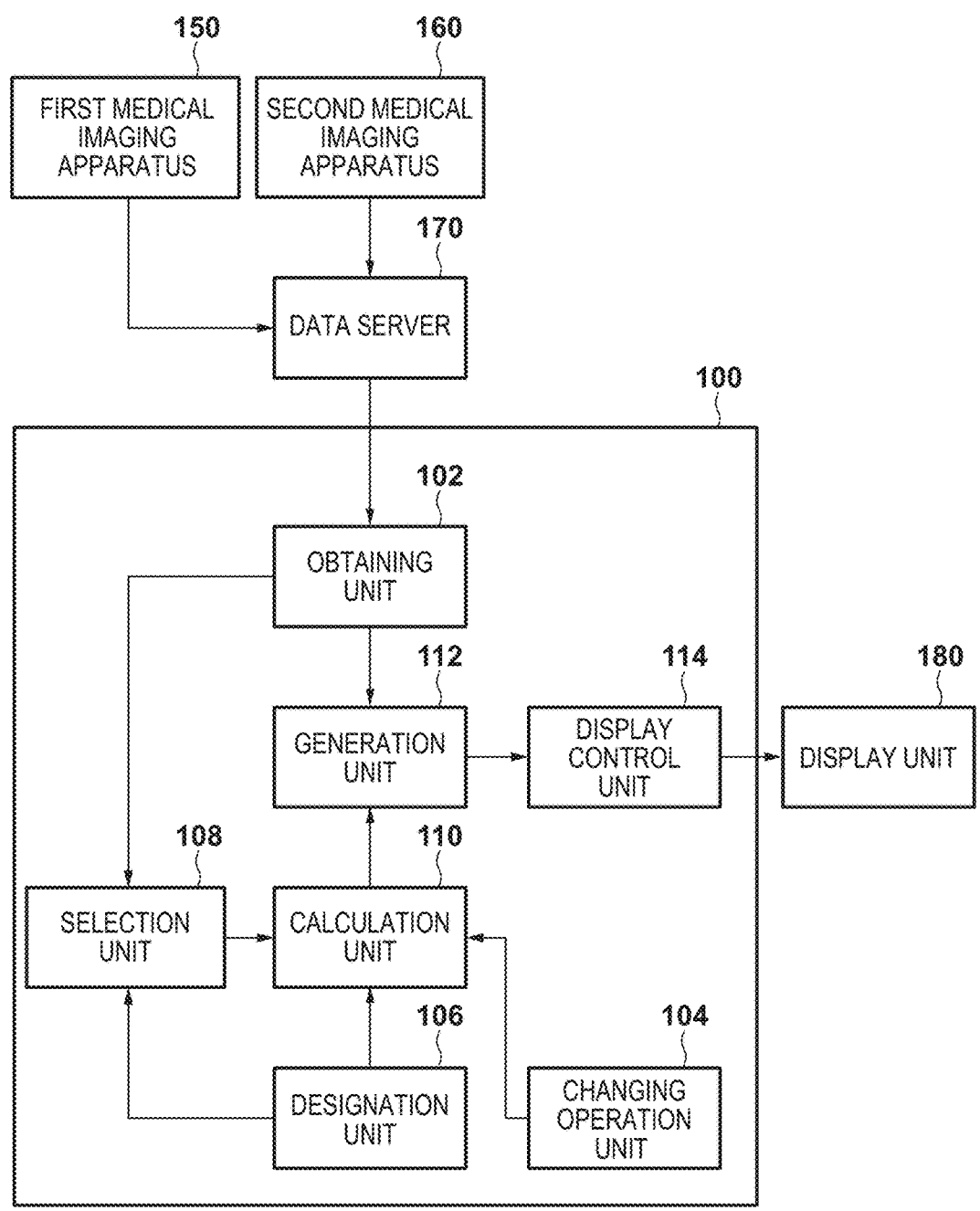
FIG. 1 is a block diagram showing the equipment configuration of an image processing apparatus according to an embodiment.

Embodiments of the present invention will be exemplarily described in detail below with reference to the accompanying drawings. Note that the constituent elements described in the embodiments are merely examples. The technical scope of the present invention is determined by the scope of claims and is not limited by the following individual embodiments.

First Embodiment

An image processing apparatus according to this embodiment includes an obtaining unit which obtains three-dimensional image data and the positions of a plurality of feature points in the three-dimensional image data and a designation unit which designates a designation point indicating a portion of interest in the three-dimensional image data. In addition, the image processing apparatus includes a selection unit which selects one or more feature points from a plurality of feature points by using information determined by the position of a designation point and the positions of the plurality of feature points, and a generation unit which generates, from the three-dimensional image data, a cross section image on the plane determined by a designation point and selected feature points. The image processing apparatus further includes a display control unit which displays the generated cross section image on the display unit.

A feature point indicates a point having a characteristic image feature on its peripheral portion in three-dimensional image data. The selection unit of the image processing apparatus can select one or more feature points from a plurality of feature points by using information determined by the position of a designation point and the positions of a plurality of feature points. For example, the selection unit can select feature points near a designation point. Alternatively, the selection unit can select two feature points from a plurality of feature points without using the position of a designation point. In this case, the selection unit may randomly select two feature points or may select feature points near the position of a reference feature point from a plurality of feature points based on the positional relationship between the plurality of feature points. Alternatively, the selection unit can select feature points from a plurality of feature points in descending order of distance from a reference feature point.

The image processing apparatus according to this embodiment has a function as an image viewer. Upon reception of two different three-dimensional image data (the first and second three-dimensional image data) obtained by imaging the same object, this function supports the operation of searching for a portion, on one three-dimensional image, which corresponds to a portion of interest on the other three-dimensional image. In addition, when a pair of points expected to correspond to each other on two different three-dimensional image data are input as designation points, the image processing apparatus performs the processing of generating a cross section image from the three-dimensional image data. That is, the image processing apparatus generates and displays, from the first three-dimensional image data, a cross section image cut out from the first three-dimensional image data along a plane (cut plane) including a designation point on the first three-dimensional image and the two feature points selected by the selection unit. In addition, this apparatus generates and displays, from the second three-dimensional image data, a cross section image cut out from the second three-dimensional image data along a plane (cut plane) including a designation point on the second three-dimensional image and points, on the second three-dimensional image, which correspond to the two feature points.

The two cross section images displayed by the image processing apparatus are images on cross sections including designation points and corresponding points (anatomically identical feature points), and hence become cross section images including image features as references for the comparison between the designation points. When the user selects feature points near a designation point, in particular, it is possible to reduce the displacement between cross sections caused by the influence of deformation. This allows the user to check, upon seeing the two cross section images, whether the designation points on the two different three-dimensional images are anatomically identical, that is, corresponding points. In addition, the user can update the designation of the position of a designation point while seeing an image. Updating the designation of the position of a designation point enables the image processing apparatus to generate and display a cross section image on a cut plane determined based on the updated designation point and feature points from each three-dimensional image data.

Note that in this embodiment, the breast is an object. However, the scope of the present invention is not limited to this portion, and other portions can be objects. The arrangement and processing of the embodiment will be described below with reference to FIGS. 1 to 4.

FIG. 1 is a block diagram showing the arrangement of a medical image diagnostic system (image processing system) according to this embodiment. As shown in FIG. 1, an image processing apparatus 100 according to the embodiment is connected to a data server 170 and a display unit 180. The image processing apparatus 100 is also connected to a first medical imaging apparatus 150 (first imaging unit) and a second medical imaging apparatus 160 (second imaging unit), which function as imaging units which obtain three-dimensional image data, via the data server 170.

The first medical imaging apparatus 150 is an MRI apparatus which obtains the first three-dimensional image data (MRI image) by imaging the breast in a prone position. The second medical imaging apparatus 160 is a CT apparatus which obtains the second three-dimensional image data (CT image) by imaging the breast in a supine position. These three-dimensional image data are stored in the data server 170. Note that modalities which obtain three-dimensional image data may include a three-dimensional ultrasonic imaging apparatus, a photoacoustic tomography apparatus, a PET/SPECT, and an OCT apparatus as well as an MRI apparatus and a CT apparatus. In addition, the first and second three-dimensional image data may be those obtained by the same modality or obtained by imaging the object in the same posture. For example, such images may be those obtained by imaging the same patient using the same modality at different dates and times for follow-up observation.

Each of the first and second three-dimensional image data held in the data server 170 (holding unit) is a tomographic image group obtained in advance by imaging the object using the MRI apparatus and the CT apparatus. Assume that the first and second three-dimensional image data are held in the data server 170 upon conversion the position and posture of each tomographic image of each three-dimensional image data into those in a reference coordinate system (a coordinate system in a space with reference to the object). The first and second three-dimensional image data expressed by the reference coordinate system are input to the image processing apparatus 100 via an obtaining unit 102. Note that in this case, a position is represented by three position components (three-dimensional position information) X, Y, and Z in the three-dimensional space of the reference coordinate system.

A posture is the degree of rotation or tilt represented by three angle components (three-dimensional angle information), namely roll, pitch, and yaw in a three-dimensional space.

In addition, the data server 170 holds the three-dimensional coordinate values of feature point group (corresponding point group) corresponding to each other in the respective three-dimensional image data. These data are also input to the image processing apparatus 100 via the obtaining unit 102. In this embodiment, the data server 170 holds the three-dimensional position information of a plurality of feature points in the reference coordinate system for each three-dimensional image data. Note that in the following description, feature points on the first and second three-dimensional images will be respectively referred to as the first and second feature points. With respect to each first feature point, the second feature point pairing with it (representing an anatomically identical point) exists. Assume that as correspondence information which makes the first feature point correspond to the second feature point, a common ID number (identification information) is assigned to the corresponding feature points. That is, assume that each feature point is represented by an ID number (identification information) of each point and three position components (three-dimensional position information) X, Y, and Z in the three-dimensional space of the reference coordinate system.

The display unit 180 displays the display image generated by the image processing apparatus 100. The display unit 180 is provided with a button for determining whether to change a cut plane, a button for determining whether to re-designate a designation point, a button for determining whether to terminate designation point designation processing, and the like.

(Arrangement of Image Processing Apparatus 100)

The image processing apparatus 100 is constituted by constituent elements described below. The obtaining unit 102 obtains the first and second three-dimensional image data as three-dimensional image data. The obtaining unit 102 obtains, as the positions of a plurality of feature points, the positions of a plurality of first feature points in the first three-dimensional image data and the positions of a plurality of second feature points in the second three-dimensional image data. In addition, the obtaining unit 102 obtains correspondence information which makes the positions of the plurality of first feature points correspond to the positions of the plurality of second feature points. The obtaining unit 102 also obtains the three-dimensional coordinate values of a feature point group on each three-dimensional image data of the first and second three-dimensional image data. Correspondence information is information which makes the three-dimensional coordinate values of feature point groups in the first and second three-dimensional image data correspond to each other. The obtaining unit 102 outputs obtained information to a selection unit 108 and a generation unit 112.

A changing operation unit 104 accepts the input made by a mouse or keyboard operation by the user. The changing operation unit 104 obtains a change parameter for changing a cut plane in one of the first and second three-dimensional image data or cut planes in both the first and second three-dimensional image data in accordance with the accepted input, and outputs the parameter to a calculation unit 110.

A designation unit 106 designates the first and second designation points in the first and second three-dimensional image data and obtains the positions of the respective designation points in the reference coordinate system in accordance with a user instruction. The designation unit 106 outputs the obtained positions of the first and second designation points to the selection unit 108 and the calculation unit 110.

The selection unit 108 selects one or more feature points from a plurality of feature points by using information determined by the position of a designation point and the positions of a plurality of feature points. Alternatively, the selection unit 108 selects two feature points from a plurality of feature points without using the position of a designation point. The selection unit 108 selects two feature points from the first feature point group based on the comparison between the position of the first designation point and the position of each first feature point in the first three-dimensional image data. For example, the selection unit 108 selects two feature points near the position of a designation point. In addition, the selection unit 108 selects a point corresponding to the selected first feature point from the second feature point group, in the second three-dimensional image data, by using correspondence information. Note that the feature points selected by the selection unit 108 include a reference point indicating a specific portion in an object.

Upon selecting the first feature point from the plurality of first feature points in the first three-dimensional image data, the selection unit 108 selects the second feature point corresponding to the selected first feature point from the plurality of second feature points based on correspondence information. Alternatively, upon selecting the second feature point from the plurality of second feature points in the second three-dimensional image data, the selection unit 108 selects the first feature point corresponding to the selected second feature point from the plurality of first feature points based on correspondence information.

The calculation unit 110 calculates, as a cut plane in the three-dimensional image data, a plane determined based on the designation point designated by the designation unit 106 and the two feature points selected by the selection unit 108 in the first and second three-dimensional image data. In addition, the calculation unit 110 changes a cut plane in one of the first and second three-dimensional image data or cut planes in both the first and second three-dimensional image data based on the change parameter obtained by the changing operation unit 104 to change a cut plane. The calculation unit 110 then outputs the calculated or changed cut plane to the generation unit 112.

The generation unit 112 cuts out two-dimensional cross section images from the first and second three-dimensional image data along the cut plane calculated or changed by the calculation unit 110, and outputs the images to a display control unit 114. For example, the generation unit 112 generates the first cross section image on the first cut plane determined based on the position of the first designation point and the position of the first feature point, and generates the second cross section image on the second cut plane determined based on the position of the second designation point and the position of the second feature point.

The display control unit 114 generates display data having two generated cross section images arranged side by side, and performs display control to cause the display unit 180 to display the display data. That is, the display control unit 114 causes the display unit 180 to display the first and second cross section images. The user checks the cross section image displayed by the display control unit 114. Upon determining that the positions of designation points designated in the respective three-dimensional image data match each other (correspond to each other), the user inputs an instruction to the image processing apparatus via a UI (not shown). If this instruction is input, the positions of the respective designation points are stored as corresponding points in the two three-dimensional image data in a storage unit (not shown) in the image processing apparatus 100, thus completing the designation point designation processing.

Figure 2A:
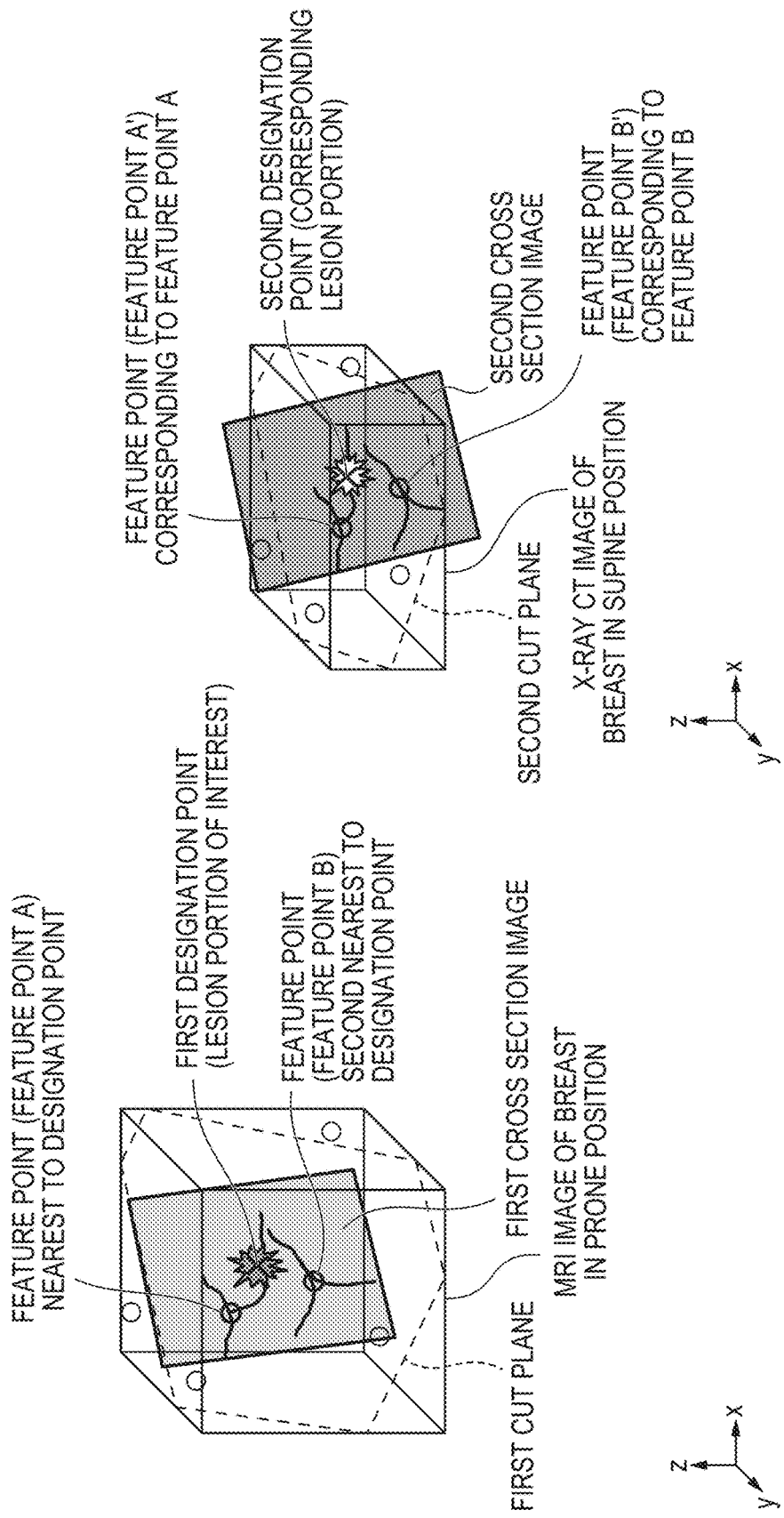
FIGS. 2A and 2B are views showing examples of cut planes and cross section images according to this embodiment.

An outline of the cross section image generation processing executed by the image processing apparatus 100 described above will be described with reference to FIGS. 2A and 2B. FIG. 2A shows the first three-dimensional image data (an MRI image of the breast in a prone position) obtained from the first medical imaging apparatus 150 and the second three-dimensional image data (a CT image of the breast in a supine position) obtained from the second medical imaging apparatus 160. These data are three-dimensional image data subjected to designation point designation processing. In addition, planes (the first and second cut planes) passing through the respective three-dimensional image data and the first and second cross section images are shown (FIG. 2B), with regions as display targets being cut out from the respective three-dimensional image data along the respective cut planes.

In addition, on the respective cross section images, a lesion portion of interest on the first three-dimensional image data and a corresponding lesion portion on the second three-dimensional image data which corresponds to the lesion portion of interest are displayed. Assume that in the respective three-dimensional image data, the positions of portions expected to be these lesion portions have been designated as the first and second designation points by the designation unit 106. Referring to FIG. 2A, the designation points are indicated by cross marks. The inside of the lesion portion of interest indicated by the designation point on the first three-dimensional image data is displayed by hatching, whereas the inside of the corresponding lesion portion on the second three-dimensional image data is displayed without hatching. The two portions are displayed in different manners to exemplarily indicate that the images obtained by imaging the same object using an MRI apparatus and a CT apparatus look different. In addition, assume that two or more characteristic positions such as a blood vessel branch portion and a mammary fat boundary portion, which can be made to correspond to each other in the respective three-dimensional data, are designated in advance as two or more feature points. Referring to FIG. 2A, a feature point group is indicated by circles.

Figure 2B:
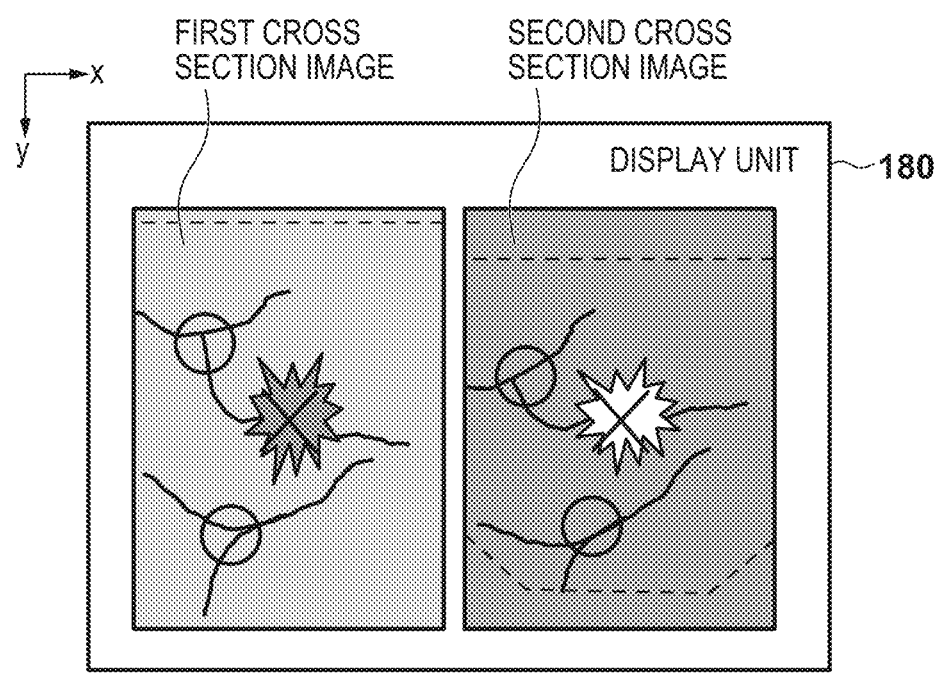

The selection unit 108 selects a feature point A nearest to the first designation point and a feature point B second nearest to the first designation point based on the positional relationship between the position of the first designation point (lesion portion of interest) and the position of each first feature point on the first three-dimensional image data. On the other hand, on the second three-dimensional image data, the selection unit 108 selects a feature point A' and a feature point B' as points corresponding to the feature points A and B from the second feature points on the second three-dimensional image data based on correspondence information. In this case, the first cut plane can be determined as a plane passing through the following three points: the first designation point, the feature point A, and the feature point B. In addition, the second cut plane can be determined as a plane passing through the following three points: the second designation point, the feature point A', and the feature point B'. FIG. 2B is a view showing a display example of the first and second cross section images cut out from the first and second three-dimensional image data along the first and second cut planes. The user can check whether a designation point is accurately designated, by multidirectionally evaluating, for example, the way how the lesion portion indicated by the designation point and the peripheral portion indicated by feature points look.

Figure 3:
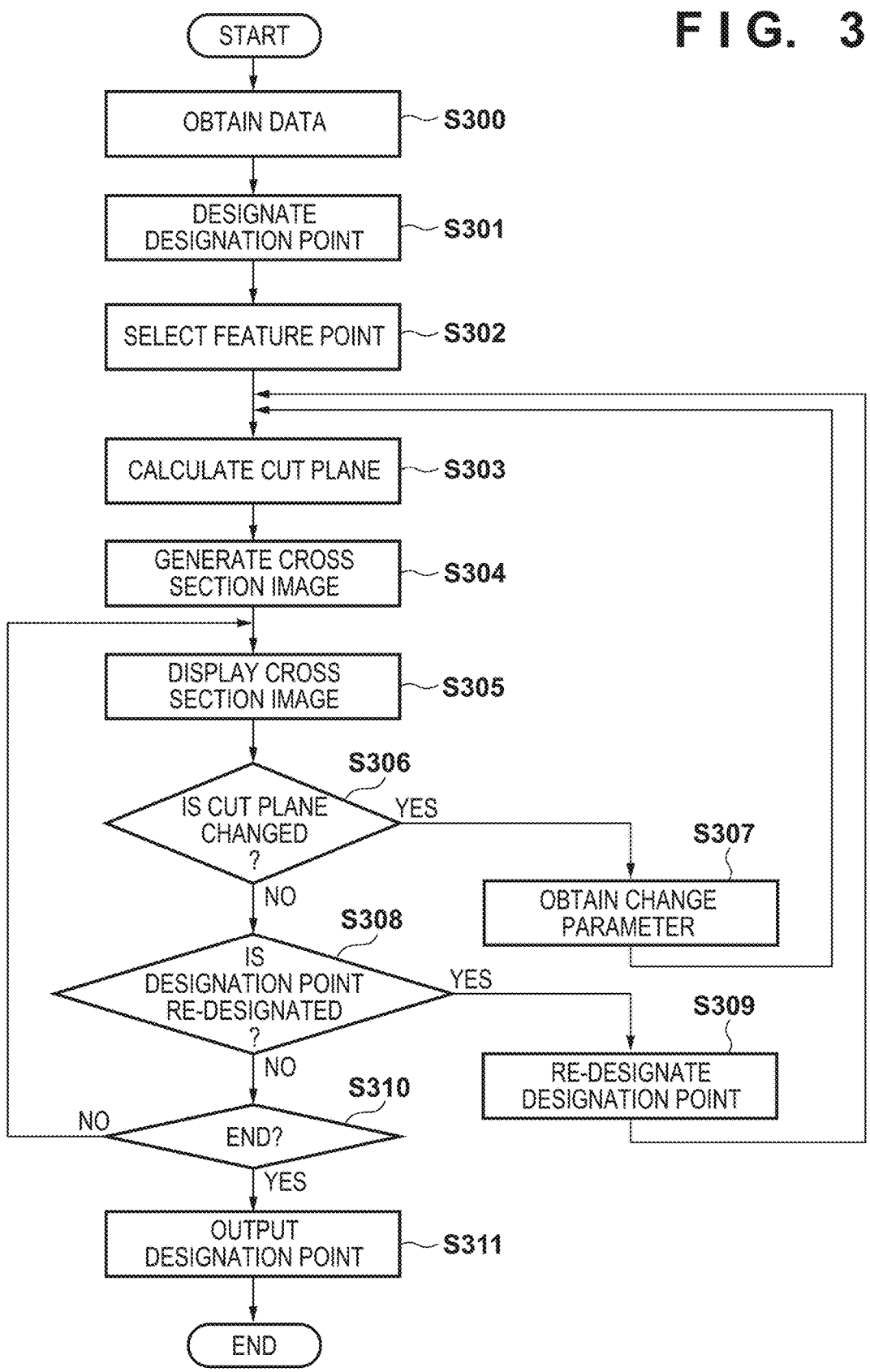
FIG. 3 is a flowchart showing an overall processing procedure in the first embodiment.

FIG. 3 is a flowchart showing an overall processing procedure performed by the image processing apparatus 100.

(Obtaining of Data)

In step S300, the obtaining unit 102 of the image processing apparatus 100 obtains the respective three-dimensional image data (the MRI image of the breast in a prone position and the CT image of the breast in a supine position) and the three-dimensional coordinate values of feature points (corresponding points) respectively corresponding to the data from the data server 170.

(Designation of Designation Point)

In step S301, the designation unit 106 of the image processing apparatus 100 obtains the position of the first designation point designated by the user on the first three-dimensional image and the position of the second designation point designated by the user on the second three-dimensional image.

More specifically, first of all, the display control unit 114 displays the respective tomographic images constituting each three-dimensional image data on the screen. It is possible to arbitrarily select a tomographic image as a display target from a tomographic image group. The changing operation unit 104 accepts a mouse or keyboard operation by the user. A tomographic image can be selectively displayed in accordance with the input. The user operates the mouse and keyboard to select and display tomographic images each expected to include a lesion portion from the tomographic image groups of the MRI image and the CT image. The user then performs an input operation to designate, as a designation point, the position of a portion expected to be lesion portion on the displayed tomographic image. In accordance with the input, the designation unit 106 obtains the positions of the first and second designation points in the reference coordinate system by using the position and posture of the tomographic image.

In this case, for example, the position of a designation point is designated in the following procedure. First of all, the display control unit 114 switches and displays tomographic images on the display unit 180 in accordance with a user instruction. When a portion expected to be a lesion portion of interest is depicted on a tomographic image, the user clicks the position of the portion expected to be the lesion portion on the display screen with the mouse or the like to designate the position of a designation point in the reference coordinate system. Note that the position of a designation point need not always be designated on a tomographic image of three-dimensional image data, but may be designated on a tomographic image obtained by cutting out three-dimensional image data along a cut plane in an arbitrary posture.

A designation point need not accurately be designated because it is for designating an initial position. In order to complete designation point designation processing in a short time, it is possible to designate a position near the center of each corresponding lesion portion. Note that since this embodiment aims at observing a lesion portion of an object, the central position of the lesion portion is designated as a designation point. However, it is possible to designate a characteristic point, other than a central position and a lesion portion, as a designation point.

Note that since both the first and second three-dimensional image data are expressed by the same reference coordinate system, the positions of the respective lesion portions in the reference coordinate system do not greatly differ from each other. For this reason, this apparatus may be configured to designate the position (initial position) of the second designation point by using the position of the first designation point in the reference coordinate system without any change instead of making the user designate.

In addition, the designation unit 106 can select the first and second designation points from the feature point group obtained by the obtaining unit 102. In this case, since a common ID number (identification information) is assigned to each feature point, selecting a feature point as a designation point in one of the first and second three-dimensional image data can determine a designation point in the other data. In this case, the feature point selected as a designation point is stored in a storage unit (not shown) as a point which is not selected by the selection unit 108. Note that the order of designation of designation points may be reversed. That is, the second designation point (for example, the central position of a lesion portion) in the second three-dimensional image data may be selected first.

(Selection of Feature Points)

In step S302, the selection unit 108 of the image processing apparatus 100 selects two feature points (first selection) from the first feature point group on the first three-dimensional image data. In this embodiment, two feature points are selected by using the information determined by the position of the first designation point and the position of each point of the first feature point group. For example, feature points are selected based on the distances between the designation point and feature points. For example, feature points located near the designation point can be selected. More specifically, the selection unit 108 selects a feature point (feature point A) nearest to the first designation point and a feature point (feature point B) second nearest to the first designation point. The selection unit 108 also selects points (feature points A' and B' in FIG. 2A) corresponding to the feature points A and B (second selection) from the second feature point group on the second three-dimensional image data based on correspondence information of feature points. Note that the selection unit 108 can also perform the first selection with respect to the second three-dimensional image data and the second selection with respect to the first three-dimensional image data. The three-dimensional image data subjected to the first selection may be selected by the user with a UI or the like or the first selection may be performed with respect to three-dimensional image data in which a designation point is designated first.

A method of selecting two feature points in the first selection is not limited to the method of selecting a feature point nearest to a designation point and a feature point second nearest to the designation point. If there is a reference point indicating a specific portion in an object, the selection unit 108 may select each feature point such that the positional relationship between the feature point, a designation point, and a reference point satisfies a predetermined condition. For example, it is possible to sequentially select feature points from a plurality of feature points based on the comparison between a straight line connecting a reference point and a designation point and the positions of the plurality of feature points in ascending order of distance from the straight line. For example, when the papilla or the like is set as a reference point, a feature point nearest to a straight line connecting the reference point and a designation point and a feature point second nearest to the straight line may be selected. In this case, consideration may also be given to the distance from the foot of a vertical line vertically extending downward from each feature point and the designation point. This makes it easier to select feature points along the running of a mammary gland from the papilla to a lesion portion. The generation unit 112 generates, from the three-dimensional image data, a cross section image on the plane determined based on the position of the designation point, the position of the reference point indicating the specific portion in the object, and the positions of the feature points selected by the selection unit 108.

Alternatively, it is possible to add a condition that feature points to be selected are limited to those whose distances from a designation point are equal to or more than a predetermined distance (that feature points too near to the designation point are not selected). This can avoid the problem that a cut plane becomes unstable when selected feature points are too near a designation point. In addition, it is possible to add a condition that the second feature point to be selected is limited to a feature point such that the angle determined by a straight line connecting a designation point and the first feature point and a straight line connecting the designation point and the second feature point falls within a predetermined range. This can avoid the problem that a cut plane becomes unstable.

In addition, the selection unit 108 can select feature points from a plurality of feature points based on the comparison between a threshold and the information determined by the position of a designation point and the positions of the plurality of points. For example, the selection unit 108 can select feature points by using the area of a plane constituted by a designation point and two feature points. For example, the selection unit 108 can select feature points from a plurality of feature points such that the area of a plane constituted by a designation point and two feature points becomes equal to or more than a predetermined value (equal to or more than an area threshold). For example, the selection unit 108 can select feature points such that the area of a triangle constituted by a designation point and two feature points becomes equal to or more than predetermined value.

In addition, the selection unit 108 can select a feature point by using the angle determined by a straight line connecting a designation point and the first feature point and a straight line connecting the designation point and the second feature point. For example, it is possible to select a feature point from a plurality of feature points such that the angle determined by a straight line connecting a designation point and the first feature point and a straight light connecting the designation point and the second feature point falls within a predetermined angle (threshold: a straight line angle threshold). For example, two feature points may be selected such that the angle determined by a straight line connecting a designation point and the first feature point and a straight line connecting the designation point and the second feature point becomes near to 90° (the absolute value of the difference between the angle and 90° becomes smaller than a predetermined angle). In this case, when the position of the designation point is slightly changed (re-designated), it is possible to prevent the angle of a cut plane from greatly changing from the angle before re-designation to result in difficulty in seeing the position of the designation point.

Alternatively, the selection unit 108 can select feature points such that the distance from a predetermined curved plane such as a body surface or pectoralis major muscle surface to a designation point becomes nearest and second nearest to the distances from the curved plane to the feature points. This makes it easier to select feature points at the same depth as that of the designation point.

In addition, the selection unit 108 can select feature points by using the angle determined by the plane determined by a designation point and two feature points and a reference plane. For example, the selection unit 108 can select feature points such that the angle determined by the plane determined by a designation point and two feature points and a predetermined reference plane becomes smaller than a predetermined angle (threshold: plane angle threshold). Alternatively, the selection unit 108 can select feature points such that the angle determined by the plane determined by a designation point and two feature points and a reference plane becomes the minimum. In this case, as a reference plane, it is possible to use an axial plane, a sagittal plane, a coronal plane, or the like. In this case, it is possible to observe a cross section image on a cross section similar to a familiar cross section generally used in medical care.

The selection unit 108 can also select feature points such that the complexity of texture in a cross section image on a plane including a designation point and two feature points becomes the highest. In this case, it is expected that image features as references for diagnosis of a lesion portion are included in a cross section image.

Figure 4A:
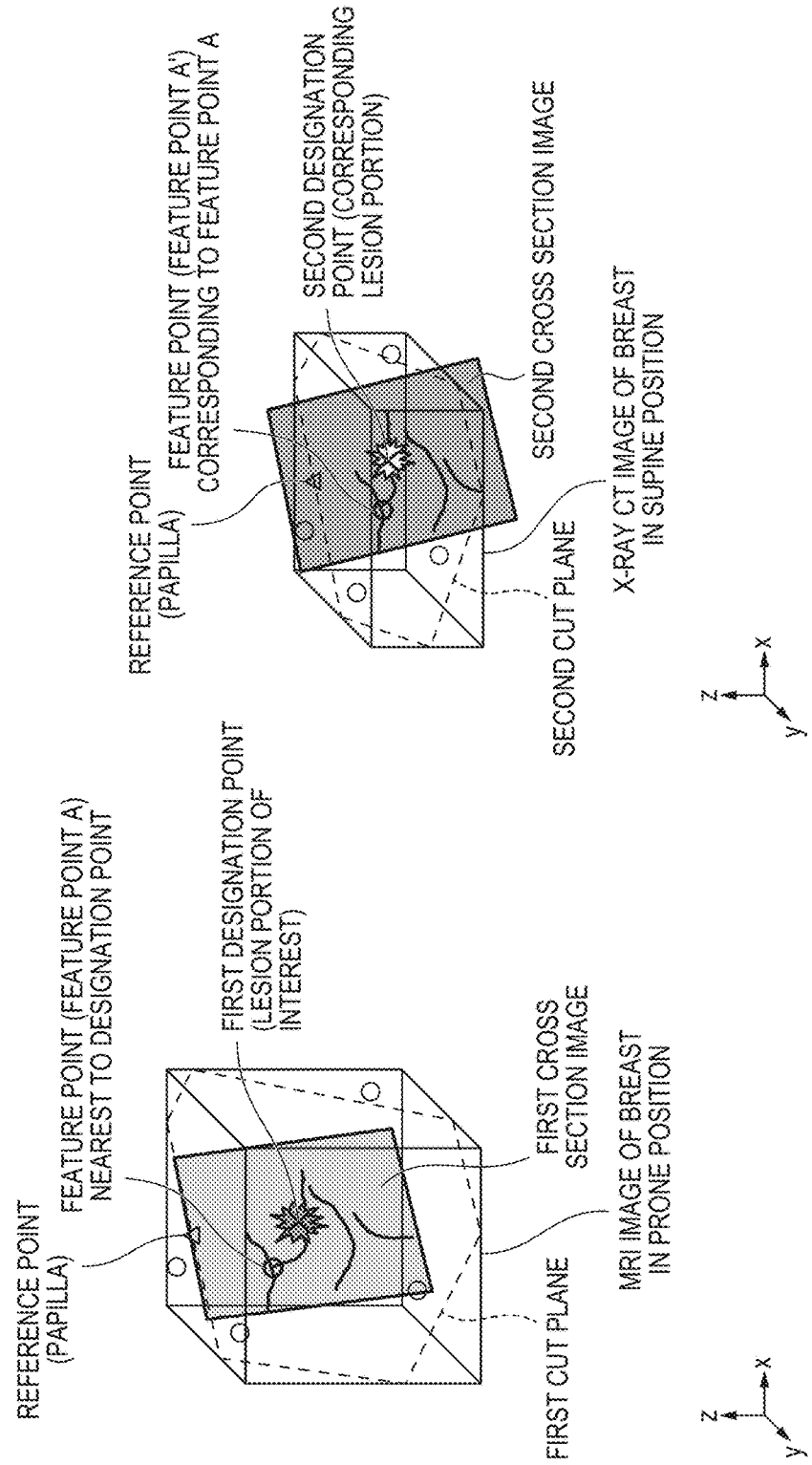
FIGS. 4A and 4B are views showing other examples of cut planes and cross section images in the embodiment.

In addition, it is possible to use, as one of two feature points, a fixed reference point designated in advance (for example, a point having an anatomical significance such as a papilla position) as shown in FIG. 4A regardless of the distance from the designation point. In this case, it is possible to select and use one of a plurality of reference points which is nearest to the designation point. In this case, it is possible to diagnose a lesion portion while checking its relationship with the reference point. At this time, it is possible to select another feature point such that the positional relationship between the reference point, the designation point, and the feature point satisfies a predetermined condition. For example, it is possible to select a feature point whose distance from a line segment connecting the reference point and the designation point falls within a predetermined range. In addition, the apparatus may be configured to allow the user to select two feature points from a plurality of candidates within a predetermined distance from a designation point with a UI or the like. Furthermore, the selection unit 108 can select two feature points from a plurality of feature points without using the position of a designation point when using a feature point selection method in the first selection. In this case, the selection unit 108 may randomly select two feature points or can select, from a plurality of feature points, feature points near to a feature point as a reference. Alternatively, the selection unit 108 can also select feature points from a plurality of feature points in descending order of distance from the position of a feature point as a reference.

(Calculation of Cut Plane)

In step S303, the calculation unit 110 of the image processing apparatus 100 determines or changes a cut plane. If the process shifts from step S302 or S309 to step S303, the calculation unit 110 determines, in each of the first and second three-dimensional image data, a cut plane determined based on the designation point designated by the designation unit 106 and the two feature points selected by the selection unit 108. Since a plane passing through three points (a designation point and two feature points) can be obtained by a known method, a detailed description of the method will be omitted.

If the process shifts from step S307 to step S303, the calculation unit 110 determines new cut planes by applying the change parameters obtained in step S307 to the cut planes calculated by the previously executed processing in step S303. In this embodiment, the calculation unit 110 applies rotation transformation about a straight line connecting two feature points as an axis to each cut plane.

(Generation of Cross Section Image)

In step S304, the generation unit 112 of the image processing apparatus 100 generates cross section images of the first and second three-dimensional image data along the respective cut planes obtained in step S303. More specifically, the generation unit 112 determines an image cutting range and the rotation axis of in-plane rotation in a cut plane, and generates a cross section image in the range. In this case, the generation unit 112 can generate a cross section image in a range in which three-dimensional image data intersects with a cut plane without limiting a cutting range. Referring to FIG. 2A, this range corresponds to the range enclosed by the dotted line. In addition, the generation unit 112 can set a cutting range based on the position of a designation point. For example, the generation unit 112 can obtain a predetermined range in a cut plane centered on the position of a designation point, and generate a cross section image in the range. Likewise, it is possible to set a cutting range based on the positions of selected feature points and a reference point. Note that this cutting range can be enlarged to include a wider range by clicking the enlargement button arranged on the display unit 180 with the mouse.

Figure 4B:
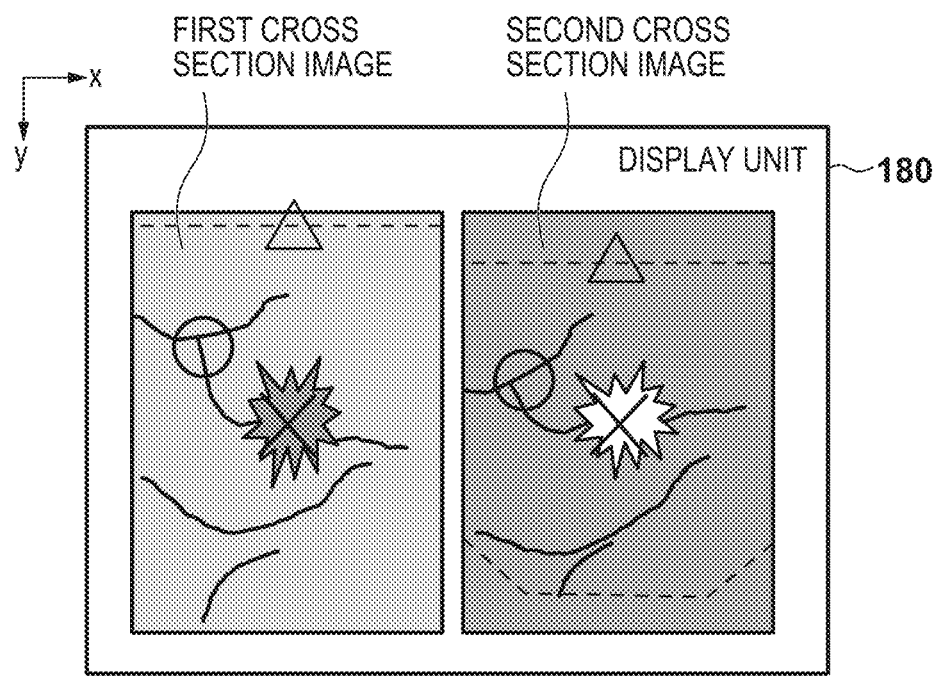

On the other hand, for example, the rotation axis of in-plane rotation may be determined so as to make the X-axis direction of the coordinate system of a cross section image intersect with the Y-axis direction (gravitational direction) of the reference coordinate system at right angles. Alternatively, the rotation axis of in-plane rotation may be determined such that a straight line connecting a designation point and a reference point coincides with the reference direction (for example, the Y-axis direction) of the coordinate system of a cross section image. FIG. 4B shows a display example in a case in which the rotation axis of in-plane rotation is determined so as to make a straight line connecting a designation point and a reference point (papilla) coincide with the Y-axis direction of the cross section image coordinate system.

Note that affine transformation may be performed for one cross section image so as to make the distances and directions from a designation point to two feature points in the first cross section image coincide with those in the second cross section image. Since an affine transformation matrix can be obtained from a combination of three points (a designation point and two feature points) before and after transformation by a known method, a detailed description will be omitted.

(Display of Cross Section Images)

In step S305, the display control unit 114 of the image processing apparatus 100 causes the display unit 180 to display two cross section images. The user as a person in charge of diagnosis sees the two cross section images and can check whether the positions of the respective designation points match lesion portions (a lesion portion of interest and a corresponding lesion portion).

The following are display examples. The display control unit 114 can respectively display the first and second cross section images on portions vertically or horizontally divided from one screen, and can also respectively display the cross section images on two screens. Alternatively, the display control unit 114 can draw the first and second cross section images in different colors and display the respective images while superimposing them, or can select and display only one of the first and second cross section images. FIG. 2B shows an example in which one screen is horizontally divided, and the first and second cross section images are displayed side by side.

In addition, the display control unit 114 can display the first and second cross section images while superimposing graphic patterns such as cross marks, squares, and circles indicating the positions of designation points and feature points on the respective images. The display control unit 114 can also perform volume rendering of one volume data and draw a graphic pattern such as a plane representing the position/posture of the other cross section image while superimposing them on each other. Furthermore, the display control unit 114 can perform display control so as to make it possible to select whether each type of graphic pattern is superimposed. FIG. 2B shows an example in which x marks representing the positions of designation points and circles representing the positions of selected feature points are superimposed and displayed.

(Change of Cut Plane)

In step S306, the image processing apparatus 100 determines whether to change a cut plane of one of the first and second three-dimensional image data or cut planes of both the first and second three-dimensional image data, and continue checking. For example, the user inputs information indicating the determination of a change by, for example, clicking the cut plane changing button (cut plane changing unit) arranged on the display unit 180 with the mouse. If information indicating the determination of a change is input, the process advances to step S307. If no information indicating the determination of a change is input, the process advances to step S308.

(Obtaining of Change Parameter for Cut Plane)

In step S307, the changing operation unit 104 obtains a change parameter for changing a cut plane of one of the first and second three-dimensional image data or cut planes of both the first and second three-dimensional image data. The process then returns to step S303. As a change parameter, the changing operation unit 104 obtains a rotation angle L around a straight line as an axis which connects two feature points. This parameter can be obtained by operating the mouse of the changing operation unit 104. For example, the changing operation unit 104 obtains the rotation angle L based on the changing operation of the changing operation unit 104 (for example, the position, movement amount, moving direction, and the like of the mouse during pressing of a button of the mouse). For example, it is possible to determine the direction vector designated by a changing operation by a series of operations of the changing operation unit 104, that is, starting a changing operation (start of pressing a button of the mouse), a moving operation (moving the mouse while pressing the button), and terminating the changing operation (releasing the button of the mouse).

The position of starting a changing operation becomes the start point of a direction vector, and the position of terminating the changing operation becomes the end point of the direction vector, thus determining the direction vector. In addition, the changing operation unit 104 can obtain, as the rotation angle L around the axis, the angle determined by this direction vector and a straight line (rotation axis) connecting the two feature points.

In this case, the changing operation unit 104 can select whether to change a cut plane of one of the first and second three-dimensional image data. For example, when the user presses the left button of the mouse, a cut plane of the first three-dimensional image can be changed. Likewise, when the user presses the right button of the mouse, a cut plane of the second three-dimensional image can be changed. When the user presses both the buttons of the mouse, cut planes of both the first and second three-dimensional images can be changed.

(Determination on whether to Re-designate Designation Point)

In step S308, the image processing apparatus 100 determines whether to re-designate a designation point in the first or second three-dimensional image data to a different designation point. If the user who has seen the cross section image displayed in step S305 determines that the image does not correspond to a designation point, he/she inputs information indicating that the designation point is re-designated. For example, the user inputs information indicating the determination of re-designation by, for example, clicking the re-designation button (re-designation unit) arranged on the display unit 180 with the mouse. If information indicating the determination of re-designation is input, the process advances to step S309. If no information indicating the determination of re-designation is input, the process advances to step S310.

(Re-designation of Designation Point)

In step S309, if an instruction to re-designate a designation point is issued, the designation unit 106 of the image processing apparatus 100 designates, in three-dimensional image data, a designation point different from the designation point designated in step S301. The designation unit 106 re-designates the position of the designation point in the first or second three-dimensional image data to the position of the different designation point. The process then returns to step S303. Each unit of the image processing apparatus 100 then performs processing similar to that in step S303 and the subsequent steps. The user can more accurately re-designate the position of a lesion portion of interest or corresponding lesion portion while observing the first and second cross section images and multidirectionally evaluating the degree of similarity between, for example, the way how the lesion portion indicated by the designation point looks and the way how the peripheral portion indicated by feature points looks.

(Determination of End of Designation Processing)

In step S310, the image processing apparatus 100 determines whether to terminate designation processing for a designation point in one of the first and second three-dimensional image data or designation points in both the first and second three-dimensional image data. The user inputs information indicating the determination of termination by, for example, clicking the end button arranged on the display unit 180 with the mouse. If it is determined that the designation processing is terminated, the process advances to step S311. If it is determined that the processing is not terminated, the process returns to step S305, and each unit of the image processing apparatus 100 performs processing similar to that in step S305 and the subsequent steps. In this case, there is no input for a change of a cut plane or no input for re-designation of a designation point, the process is set in a standby state while the cross section image is displayed until an input of termination is received, and an input is accepted.

(Output of Designation Point)

In step S311, the image processing apparatus 100 stores the positions of designation points as corresponding points in two three-dimensional image data in a storage unit (not shown). In addition, the display control unit 114 outputs the information of the corresponding designation points to the display unit 180 and causes the display unit 180 to display the corresponding information. With the above operation, the processing executed by the image processing apparatus 100 is terminated.

The image processing apparatus according to this embodiment can generate and display a cross section image on the cut plane determined based on the designation point determined with respect to a lesion portion in each of two three-dimensional image data and the two feature points selected based on the positional relationship with the designation point. With this operation, cross section images including image features as references for the comparison between the designation points are displayed. This makes it possible to properly designate the positions of corresponding points in a plurality of three-dimensional image data, thereby supporting diagnosis of the lesion portion.

Note that this embodiment has exemplified the case in which designation processing is executed for a given pair of designation points. However, when the user wants to execute designation processing for a plurality of pairs of designation points as in a case in which a plurality of lesion portions exist, the processing from step S301 to step S311 may be repeated.

Note that this embodiment has exemplified the case in which two feature points are selected from a plurality of feature points. However, this is not exhaustive, and three or more feature points may be selected. In this case, a plane including selected feature points and a designation point becomes a curved plane, and hence a cross section image (curved cross section image) on the curved plane as a cut plane may be displayed.

Second Embodiment

Figure 5:
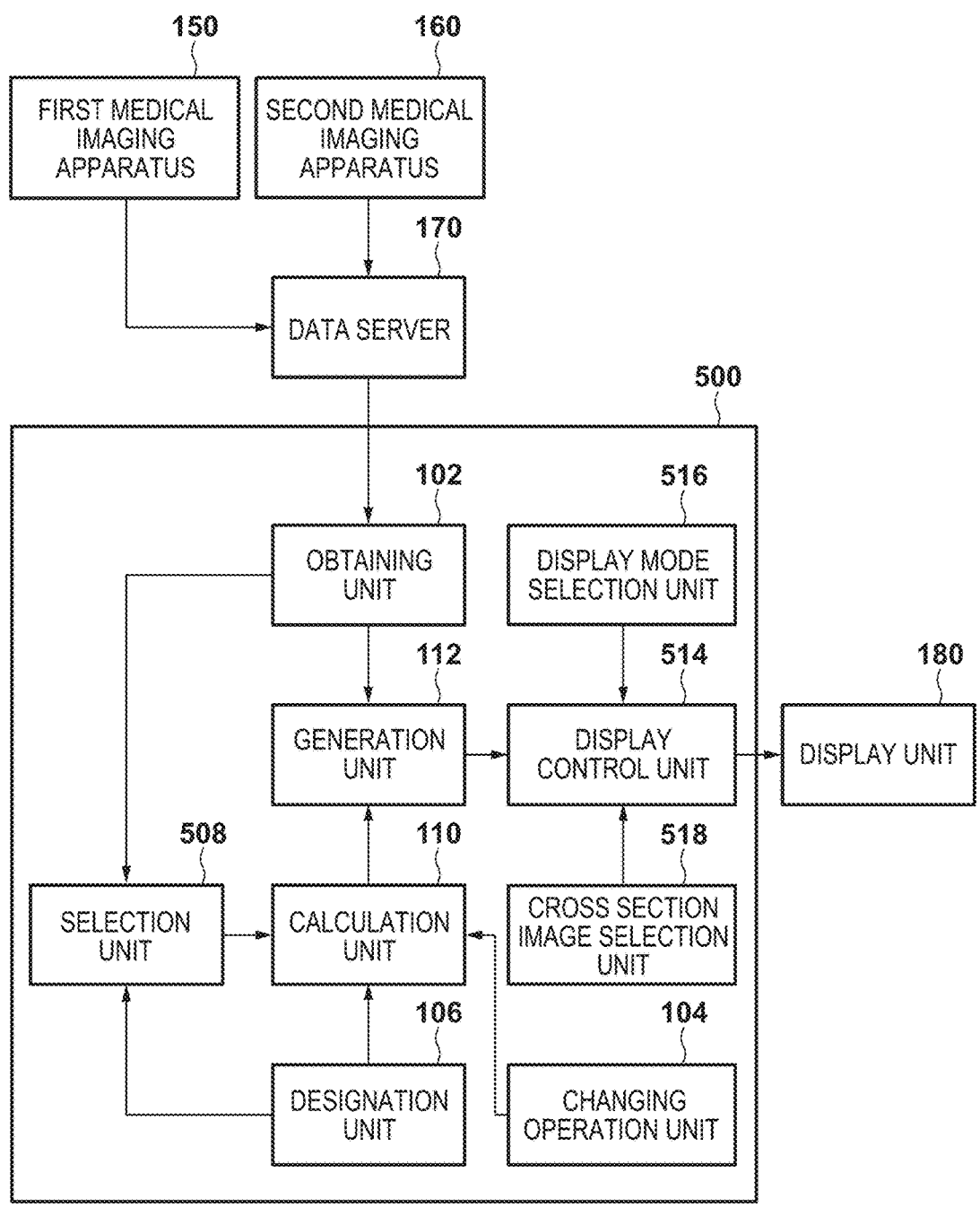
FIG. 5 is a block diagram showing the equipment configuration of an image processing apparatus according to an embodiment.

This embodiment will exemplify an arrangement configured to determine a selection order in accordance with a reference (rule) for selecting one or more feature points and sequentially select feature points based on the determined selection order. An image processing apparatus according to the second embodiment will be described below with reference to differences from the first embodiment. FIG. 5 shows the arrangement of a medical image diagnostic system (image processing system) according to the second embodiment. The same reference numerals and symbols as in FIG. 1 denote the same parts in FIG. 5, and a description of redundant portions will be omitted.

The image processing apparatus according to this embodiment includes an obtaining unit which obtains three-dimensional image data and the positions of a plurality of feature points in the three-dimensional image data, and a designation unit which designates a designation point indicating a portion of interest in three-dimensional image data. The image processing apparatus also includes a selection unit which selects one or more feature points used for the generation of a cross section image of three-dimensional image data from a plurality of feature points based on a determined selection order. In addition, the image processing apparatus includes a generation unit which generates a cross section image on the plane determined based on a designation point and selected feature points from three-dimensional image data, and a display control unit which causes the display unit to display the generated cross section image.

A selection unit 508 according to this embodiment determines a selection order in accordance with a reference (rule) for selecting feature points. The selection unit 508 then sequentially selects two feature points from a feature point group in the first or second three-dimensional image data based on the determined selection order, and outputs the selected points to a calculation unit 110.

A display mode selection unit 516 selects one of a pair display mode (first display mode) of arranging a pair of cross section images and a tiled display mode (second display mode) of arranging a plurality of pairs of cross section images in a tiled pattern, and outputs the corresponding information to a display control unit 514. The display control unit 514 controls display of cross section images in accordance with the selected display mode.

In accordance with an operation input for selecting a pair of cross section images, a cross section image selection unit 518 selects a pair of cross section images from a plurality of pairs of cross section images displayed in a tiled pattern. When the cross section image selection unit 518 selects a pair of cross section images, the display mode selection unit 516 switches the display mode from the tiled display mode to the pair display mode, and the display control unit 514 controls display of the cross section images in accordance with the switching operation.

The display control unit 514 performs display control to generate display data of a pair of cross section images arranged side by side or display data of many pairs of cross section images arranged in a tiled pattern in accordance with the display mode and cause a display unit 180 to display the generated data.

Figure 6A:
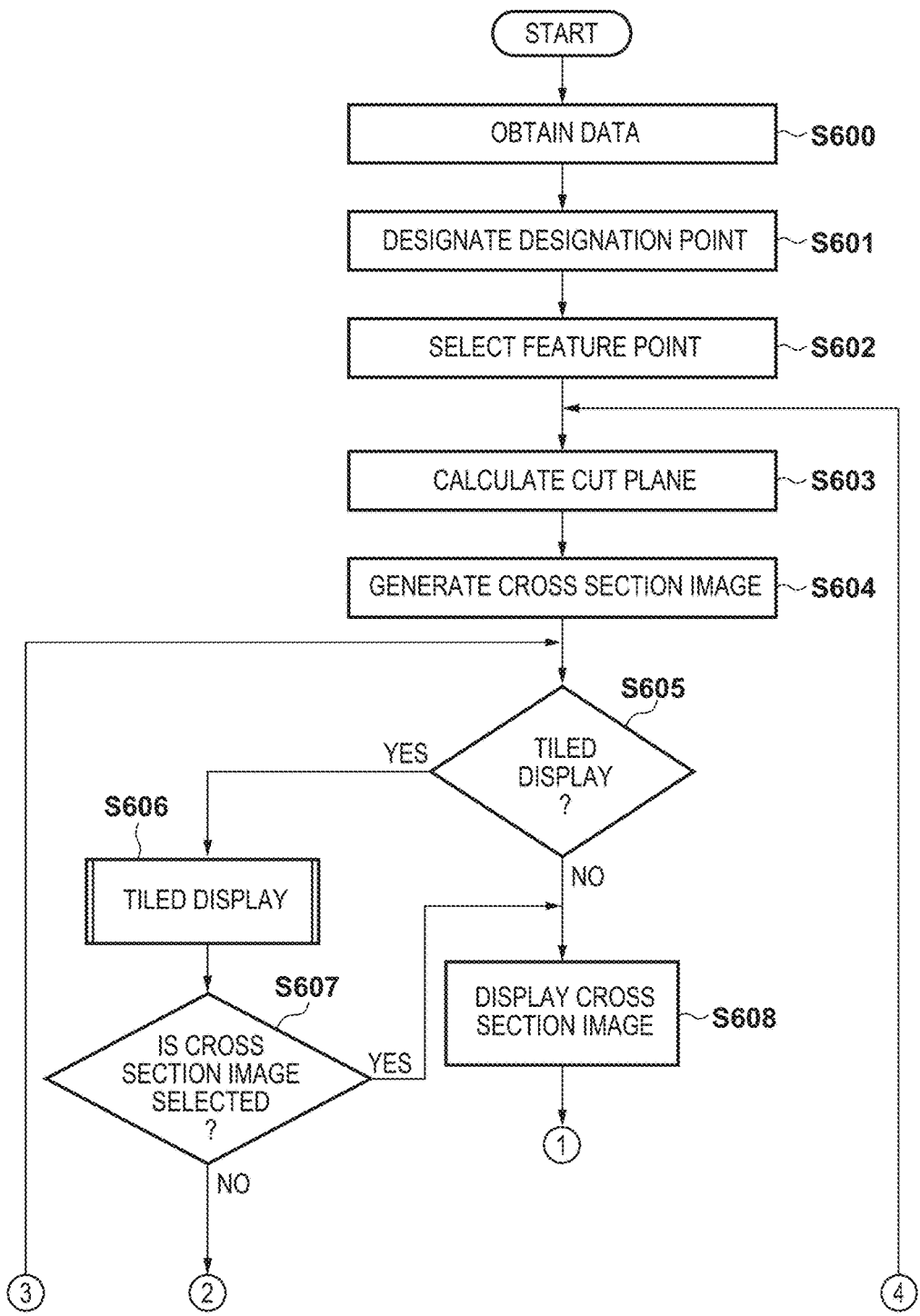
FIGS. 6A and 6B are flowcharts showing an overall processing procedure in the embodiment.
Figure 6B:
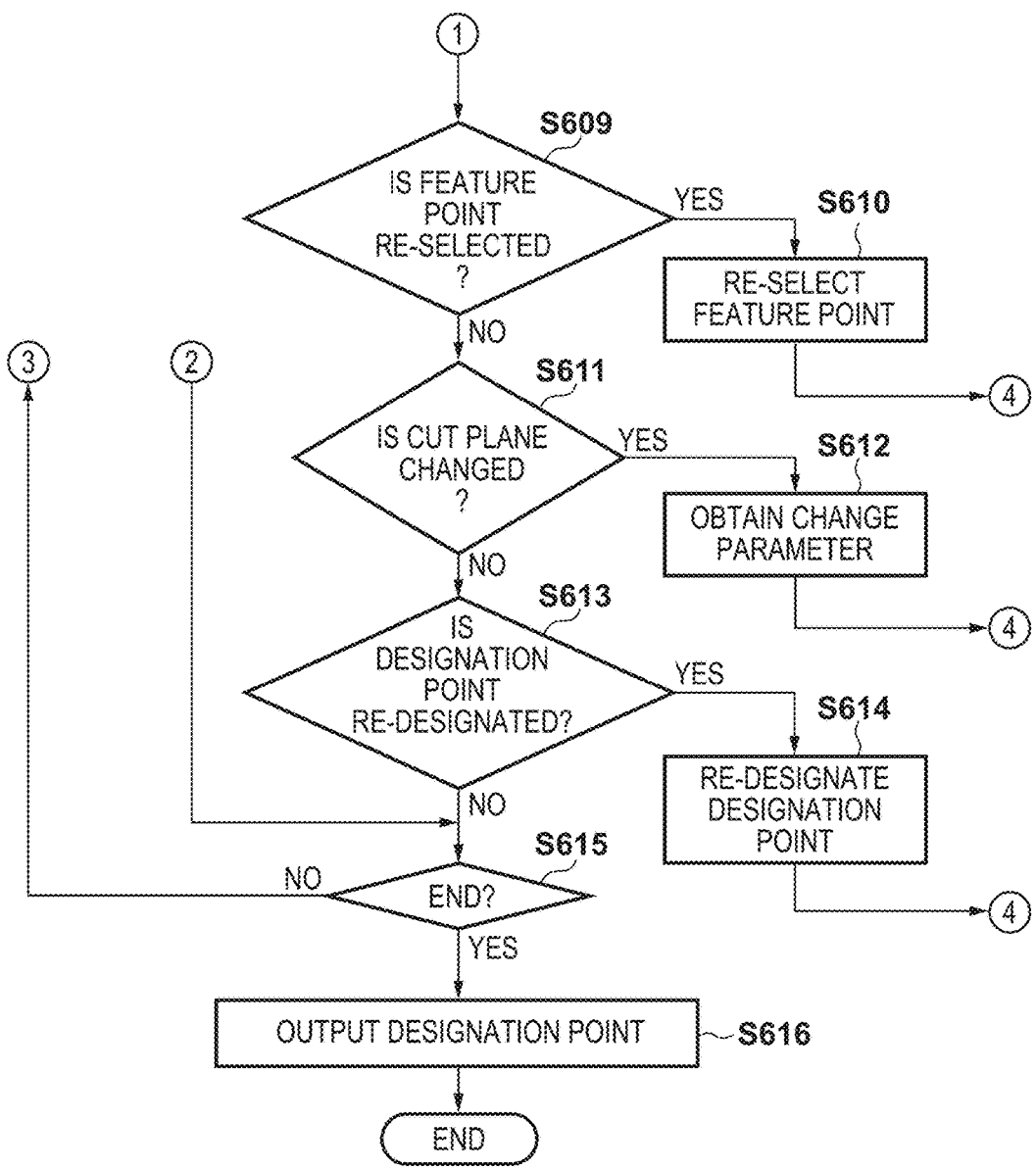

FIGS. 6A and 6B are flowcharts showing an overall processing procedure performed by an image processing apparatus 500. Since processing in steps S600, S608, and steps S611 to S616 overlaps the processing in steps S300, S305, and steps S306 to S311 in FIG. 3 in the first embodiment, a description of the processing will be omitted.

(Selection of Feature Points)

In step S602, the selection unit 508 of the image processing apparatus 500 determines a selection order in accordance with a reference (rule) for selecting feature points. The selection unit 508 then selects two feature points from a feature point group in the first three-dimensional image data or the second three-dimensional image data based on the determined selection order. In this case, it can be determined, in the same manner as in the first embodiment, which one of the first and second three-dimensional image data is used for the selection of feature points.

The selection unit 508 determines an order of selection of two feature points from a plurality of feature points based on the positional relationship based on the comparison between the position of a designation point and the positions of a plurality of feature points. For example, the selection unit 508 can sequentially select feature points from a plurality of feature points in ascending order of distance from the position of a designation point based on the determined selection order. Alternatively, the selection unit 508 can sequentially select feature points from a plurality of feature points in descending order of distance from the position of a designation point based on the determined selection order.

In this step, feature points are sequentially rearranged by using the positional relationship between the position of a designation point and the positions of a plurality of feature points as a reference for the determination of a selection order. For example, feature points are sequentially rearranged in ascending or descending order of distance from a designation point. A selection number N of a feature point is initialized to 1, and the Nth and (N+1)th feature points, that is, the first and second feature points, are selected.

As a reference for determining a selection order, in addition to the positional relationship between the position of a designation point and the positions of a plurality of feature points, the selection unit 508 can select a reference point indicating a specific portion in an object and a feature point based on the comparison of a positional relationship using a predetermined feature point. For example, feature points may be rearranged in ascending or descending order of distance from a reference point such as the papilla or a predetermined feature point. Alternatively, feature points may be rearranged in ascending or descending order of distance from a predetermined curved plane such as an object surface or pectoralis major muscle surface as a reference point indicating a specific portion in the object.

When using a reference point indicating a specific portion in an object, the selection unit 508 determines an order of selection of two feature points from a plurality of feature points based on the positional relationship between the reference point indicating the specific portion in the object and the positions of a plurality of feature points. The selection unit 508 can sequentially select feature points from a plurality of feature points in ascending order of distance from the position of the reference point based on the determined order. Alternatively, the selection unit 508 can sequentially select feature points from a plurality of feature points in descending order of distance from the position of the reference point based on the determined order.

When using a predetermined feature point, the selection unit 508 determines an order of selection of one or more feature points from a plurality of feature points based on the positional relationship between a plurality of feature points. The selection unit 508 can sequentially select two feature points from a plurality of feature points in ascending order of distance from the position of the feature point as a reference based on the determined order. Alternatively, the selection unit 508 can sequentially select two feature points from a plurality of feature points in descending order of distance from the position of the feature point as a reference based on the determined order.

Alternatively, a random order may be used as a reference for the determination of a selection order. In this case, feature points may be randomly rearranged. Note that the order (ascending or descending order) of the ID numbers (identification information) of feature points may be used as a reference for the determination of a selection order. In this case, feature points need not be rearranged.

In this case, when the selection unit 508 selects two first feature points from a plurality of first feature points, the selection unit 508 selects two second feature points corresponding to the first feature points from a plurality of second feature points based on correspondence information. In contrast to this, when the selection unit 508 selects two second feature points from a plurality of second feature points, the selection unit 508 selects two first feature points corresponding to the second feature points from a plurality of first feature points based on correspondence information.

(Calculation of Cut Planes)

In step S603, the calculation unit 110 of the image processing apparatus 500 determines or changes a cut plane. If the process shifts from step S602, S610, or S614 to step S603, the calculation unit 110 determines the cut plane determined by the designation point designated by the designation unit 106 and the two feature points selected by the selection unit 508 in each of the first and second three-dimensional image data.

In contrast, if the process shifts from step S612 to step S603, the calculation unit 110 determines a new cut plane by applying the change parameter obtained in step S612 to the cut plane calculated by the processing previously executed in step S603.

(Generation of Cross Section Images)

In step S604, a generation unit 112 of the image processing apparatus 500 sequentially generates, from three-dimensional image data, cross section images on planes each determined based on a designation point and sequentially selected feature points. The display control unit 514 causes the display unit 180 to display the sequentially generated cross section images upon arranging them.

(Determination of Display Mode)

In step S605, the display mode selection unit 516 of the image processing apparatus 500 determines first whether to change the display mode, and then determines whether the display mode is the tiled display mode. First of all, when wanting to change the display mode, the user inputs information indicating the change of the display mode. For example, the user inputs information indicating the change of the display mode by clicking the display mode changing button (display mode changing unit) arranged on the display unit 180 with the mouse. When information indicating the determination of the change of the display mode is input, the display mode selection unit 516 changes the display mode to the pair display mode if the display mode is the tiled display mode. In contrast to this, if the display mode is the pair display mode, the display mode selection unit 516 changes the display mode to the tiled display mode. On the other hand, when no information indicating the determination of the change of the display mode is input, the display mode selection unit 516 does not change the display mode.

If the display mode is the tiled display mode, the process advances to step S606. In contrast to this, if the display mode is not the tiled display mode (is the pair display mode), the process advances to step S608.

(Tiled Display)

In step S606, the display control unit 514 of the image processing apparatus 500 generates (tiles) display data with pairs of cross section images equal in number to pairs of feature points being arranged in a tiled pattern, and causes the display unit 180 to display the display data. When the display mode selection unit 516 selects the tiled display mode, the display control unit 514 causes the display unit 180 to collectively display the sequentially generated cross section images. The user as a person in charge of diagnosis sees the cross section images arranged in a tiled pattern and can check whether the positions of the respective designation points match the positions of lesion portions (a lesion portion of interest and a corresponding lesion portion). The details of tiling processing will be described later with reference to the flowchart shown in FIG. 7.

(Selection of Cross Section Images)

In step S607, the cross section image selection unit 518 of the image processing apparatus 500 determines whether to select a pair of cross section images of interest from the plurality of pairs of cross section images displayed in a tiled pattern. When the cross section image selection unit 518 selects a pair of cross section images, the display mode selection unit 516 switches the display mode from the tiled display mode to the pair display mode, and the display control unit 514 controls display of the cross section images selected in accordance with the switching operation. That is, when the user, who has seen the plurality of pairs of cross section images displayed in a tiled pattern, determines that he/she wants to observe the details of a pair of cross section images of interest, he/she inputs information indicating the selection of a pair of cross section images. For example, the user inputs information indicating the determination of selection by, for example, clicking the cross section images of interest of the cross section images displayed in a tiled pattern on the display unit 180 with the mouse. If information indicating the determination of selection is input, the display mode is switched to the pair display mode, and the selected pair of cross section images are output to the display control unit 514. The process then advances to step S608. If no information indicating the determination of selection is input, the process advances to step S616.

(Determination on Whether to Re-select Feature Points)

In step S609, the image processing apparatus 500 determines whether to re-select feature points. That is, if the user, who has seen the cross section images displayed in step S608, determines that he/she wants to see cross section images including other feature points, he/she inputs information indicating the re-selection of feature points. For example, the user inputs information indicating the determination of re-selection by, for example, clicking a re-selection button (re-selection unit) arranged on the display unit 180 with the mouse. If information indicating the determination of re-selection is input, the process advances to step S610. In contrast to this, if no information indicating the determination of re-selection is input, the process advances to step S611.

(Re-selection of Feature Points)

In step S610, if a feature point selection number N is smaller by 2 or more than a feature point count M, the selection unit 508 of the image processing apparatus 500 adds 1 to N and initializes N to 1 if otherwise. The selection unit 508 then selects the Nth and (N+1)th feature points. The image processing apparatus 500 executes the processing in the above manner.

(Tiling Processing Procedure)

Figure 7:
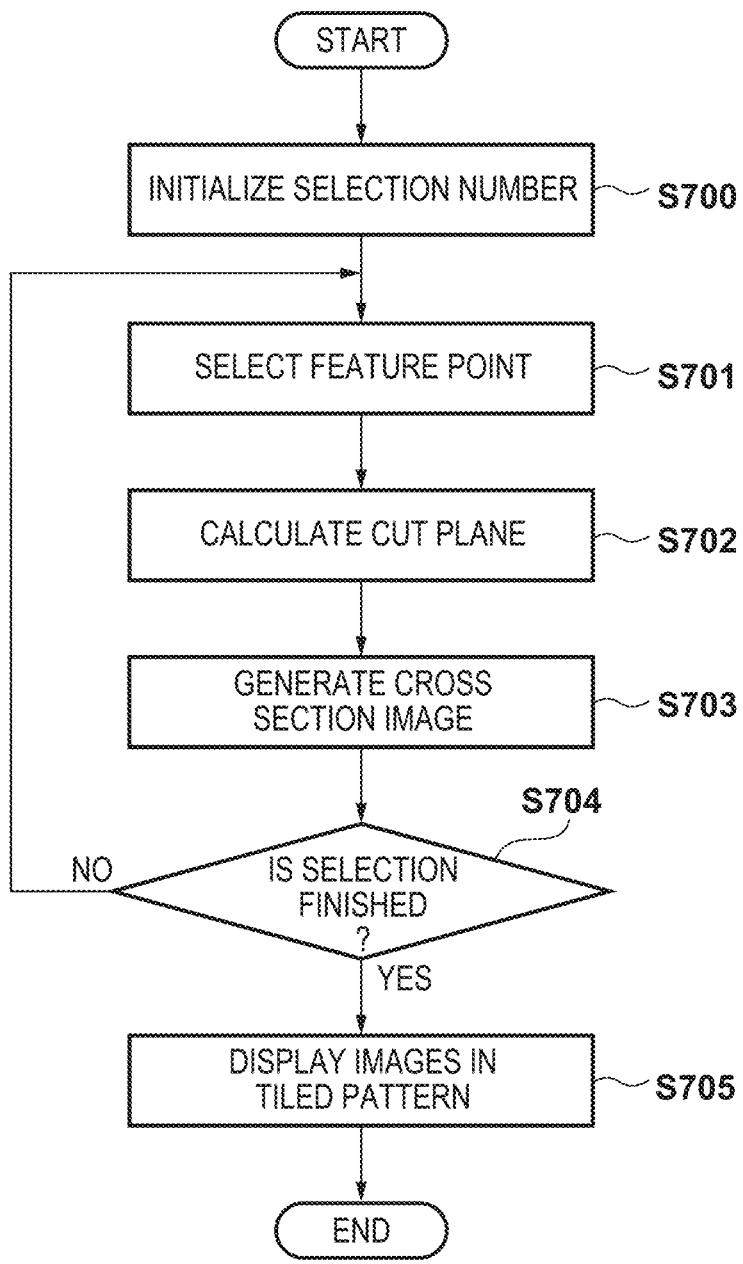
FIG. 7 is a flowchart showing a procedure for tiling processing in the embodiment.

FIG. 7 is a flowchart showing a tiling processing procedure performed by the image processing apparatus 500. The processing performed by each unit of the image processing apparatus 500 will be described below.

(Initialization of Selection Number)

In step S700, the selection unit 508 of the image processing apparatus 500 initializes the feature point selection number N to 1.

(Selection of Feature Points)

In step S701, the selection unit 508 of the image processing apparatus 500 selects the Nth and (N+1)th feature points from the feature point group rearranged based on a reference (rule) for the selection of feature points (for example, in ascending order of distance from a designation point).

(Calculation of Cut Plane)

In step S702, the calculation unit 110 of the image processing apparatus 500 determines the cut plane determined based on the designation point designated by the designation unit 106 and the two feature points selected by the selection unit 508.

(Generation of Cross Section Images)

In step S703, the generation unit 112 of the image processing apparatus 500 generates cross section images of the first and second three-dimensional image data along the cut planes determined by the calculation unit 110, and outputs the images to the display control unit 114.

(Determination of End of Feature Point Selection)

In step S704, the selection unit 508 of the image processing apparatus 500 determines whether to terminate the selection of feature points. If the feature point selection number N is smaller by 2 or more than the feature point count M, 1 is added to N, and process returns to step S701; otherwise, the selection unit 508 determines that the selection of feature points is terminated. The process then advances to step S705.

(Tiled Display)

In step S705, the display control unit 514 of the image processing apparatus 500 performs control to generate display data with (M−1) pairs of cross section images being arranged in a tiled pattern and cause the display unit 180 to display the data. The following are display examples. The display control unit 514 can divide, for example, the display area of one screen into (M−1) partial display areas in a tiled pattern and display the respective pairs of the first and second cross section images in the respective partial display areas. Alternatively, the display control unit 514 can draw the first and second cross section images in different colors and display the superimposed images in a tiled pattern. The display control unit 514 can also display only selected one of the first and second cross section images and display the selected image in tiled partial display areas. In addition, the display control unit 514 can superimpose and display various types of graphic patterns on the respective cross section images. With the above processing, the tiling processing executed by the image processing apparatus 500 is terminated.

The image processing apparatus according to this embodiment can generate and display a cross section image on the cut plane determined by the designation point designated with respect to a lesion portion in each of two three-dimensional image data and two sequentially selected feature points. This can support diagnosis of the lesion portion.

Third Embodiment

The first and second embodiments have exemplified the arrangements configured to select two feature points. However, the number of feature points to be selected is not limited to two. The third embodiment will exemplify an arrangement configured to select one feature point based on a positional relationship with a designation point. An image processing apparatus according to this embodiment will be described with reference to differences from the first embodiment. Although the arrangement of a medical image diagnostic system (image processing system) according to the third embodiment is the same as that shown in FIG. 1, the contents of processing performed by a selection unit 108 and a calculation unit 110 differ from those in the first and second embodiments.

The selection unit 108 selects one feature point based on a positional relationship with the designation point designated by a designation unit 106, and outputs the feature point to the calculation unit 110. For example, the selection unit 108 selects one feature point from the first feature point group based on the comparison (positional relationship) between the position of the first designation point and the position of each first feature point in the first three-dimensional image data. For example, the selection unit 108 selects a feature point nearest to the first designation point. In addition, the selection unit 108 selects a point corresponding to the selected first feature point from the second feature point group in the second three-dimensional image data by using correspondence information. The selection unit 108 then outputs the feature point to the calculation unit 110.

The calculation unit 110 calculates a cut plane determined based on the designation point designated by the designation unit 106 and one feature point selected by the selection unit 108 in the first and second three-dimensional image data. The calculation unit 110 changes the cut plane of one of the first and second three-dimensional image data or the cut planes of both the first and second three-dimensional image data based on the change parameter for changing the cut plane, which is obtained by a changing operation unit 104.

The calculation unit 110 then outputs the calculated or changed cut plane to the generation unit 112.

The overall processing procedure performed by the image processing apparatus 100 is the same as that in the flowchart shown in FIG. 3 except for the contents of processing in steps S302, S303, and S307.

(Selection of Feature Point)

In step S302, the selection unit 108 selects one feature point (first selection) from the first feature point group on the first three-dimensional image data. In this embodiment, one feature point (for example, a feature point A) nearest to the first designation point is selected. In addition, the selection unit 108 selects a point (for example, a feature point A' in FIG. 2A) corresponding to the feature point A (second selection) from the second feature point group on the second three-dimensional image data based on correspondence information about feature points. Note that the method of selecting a feature point in the first selection is not limited to the method of selecting a feature point nearest to a designation point, and various methods described in step S302 in the first embodiment can be used.

(Calculation of Cut Plane)

In step S303, the calculation unit 110 determines or changes the cut plane. If the process shifts from step S302 or S309 to step S303, the calculation unit 110 determines, in each of the first and second three-dimensional image data, the cut plane determined by the designation point designated by the designation unit 106 and one feature point selected by the selection unit 108. A plane passing through two points (a designation point and one feature point) may be calculated as follows. The calculation unit 110 may set in advance a reference direction (for example, the Y-axis direction representing the barycentric direction) of a reference coordinate system (a coordinate system in a space with reference to an object) and calculate, as a cut plane, a plane including a designation point and one selected feature point and a normal perpendicular to the reference direction.

If the process shifts from step S307 to step S303, the calculation unit 110 applies, to each cut plane, rotation transformation about a straight line connecting the designation point designated by the designation unit 106 and one feature point selected by the selection unit 108 as an axis.

(Obtaining of Change Parameters for Cut Plane)

In step S307, the changing operation unit 104 obtains change parameters for changing a cut plane. The calculation unit 110 can change a cut plane of three-dimensional image data by changing a rotation angle based on the change parameters. The changing operation unit 104 obtains a direction vector D of a rotation axis and a rotation angle L around the axis as change parameters. For example, the changing operation unit 104 obtains the direction vector D of the rotation axis and the rotation angle L based on the changing operation of the changing operation unit 104 (for example, the position, movement amount, moving direction, and the like of the mouse during the pressing of a button of the mouse). For example, it is possible to determine the direction vector D by a series of operations of the changing operation unit 104, that is, starting a changing operation (starting pressing a button of the mouse), a moving operation (moving the mouse while pressing the button), and terminating the changing operation (releasing the button of the mouse). The position of starting a changing operation becomes the start point of the direction vector D, and the position of terminating the changing operation becomes the end point of the direction vector D, thus determining the direction vector D. In addition, the changing operation unit 104 can obtain, as the rotation angle L around the axis, the angle determined by the direction vector D and a straight line (rotation axis) connecting the designation point designated by the designation unit 106 and one feature point selected by the selection unit 108.

Note that in cross section image generation processing in step S304, a generation unit 112 can apply enlargement, reduction, and rotation transformation to one of the first and second cross section images such that the distance and direction from a designation point to one feature point in the first cross section image coincide with those in the second cross section image.

According to this embodiment, it is possible to generate and display cross section images on cut planes each including the designation point determined with respect to a lesion portion in each of the two three-dimensional image data and one feature point selected based on a positional relationship with the designation point, with the respective reference directions matching each other.

Modification

Although each of the first to third embodiments has exemplified the case in which the two different three-dimensional image data obtained by imaging the same object are processing targets, three or more three-dimensional image data may be processed. In addition, these three-dimensional image data may be obtained by different modalities or partially or totally obtained by the same modality. This modification allows the user to compare lesion portions in three or more three-dimensional image data, and hence can support diagnosis of the lesion portion more accurately.

Fourth Embodiment

Each of the first to third embodiments has exemplified the case in which the two different three-dimensional image data obtained by imaging the same object are processing targets. However, the number of three-dimensional image data is not limited to two. The fourth embodiment will exemplify a case in which one three-dimensional image data, that is, only the first three-dimensional image data, is obtained and used. The image processing apparatus according to this embodiment will be described with reference to differences from the first embodiment.

The arrangement of a medical image diagnostic system (image processing system) according to this embodiment is the same as that shown in FIG. 1. Note, however, that one of the medical imaging apparatuses is not used. This embodiment will exemplify an arrangement which uses a first medical imaging apparatus 150 (first imaging unit) but does not use a second medical imaging apparatus 160 (second imaging unit). The medical imaging apparatus to be used is not limited to this example. It is possible to use an arrangement which uses the second medical imaging apparatus 160 but does not use the first medical imaging apparatus 150.

In addition, the contents of processing performed by each unit constituting the image processing apparatus differ from those in the above embodiments. The contents of processing performed by each unit will be described specifically below.

A data server 170 (holding unit) holds the tomographic image group obtained by imaging an object in advance using an MRI apparatus as the first three-dimensional image data. The data server 170 also holds the three-dimensional coordinate values of a feature point group in three-dimensional image data. However, no ID number (identification information) is required for a feature point. That is, assume that each feature point is represented by three position components (three-dimensional position information) X, Y, and Z in the three-dimensional space of a reference coordinate system.

An obtaining unit 102 obtains the first three-dimensional image data and the three-dimensional coordinate values of a feature point group which are input to an image processing apparatus 100, and outputs the obtained information to a selection unit 108 and a generation unit 112.

A changing operation unit 104 accepts the input made by a mouse or keyboard operation by the user, obtains a change parameter for changing a cut plane of the first three-dimensional image data in accordance with the accepted input, and outputs the obtained change parameter to a calculation unit 110.

A designation unit 106 designates, for example, the central position of a portion expected to be a lesion portion (a lesion portion of interest) in the first three-dimensional image data as the first designation point in accordance with a user instruction, and can obtain the designated point as the position of the first designation point in a reference coordinate system. The designation unit 106 outputs the position of the obtained first designation point to the selection unit 108 and the calculation unit 110.

The selection unit 108 selects two feature points from the first feature point group in the first three-dimensional image data based on the positional relationship based on the comparison between the position of the first designation point and the position of each first feature point, and outputs the selected points to the calculation unit 110.

The calculation unit 110 calculates the cut plane determined based on the designation point designated by the designation unit 106 and the two feature points selected by the selection unit 108 in the first three-dimensional image data. The calculation unit 110 also changes a cut plane of the first three-dimensional image data based on the change parameter for changing the cut plane, which is obtained by the changing operation unit 104. The calculation unit 110 outputs the calculated or changed cut plane to the generation unit 112.

The generation unit 112 cuts out a two-dimensional cross section image from the first three-dimensional image data along the cut plane calculated or changed by the calculation unit 110 and outputs the resultant image to a display control unit 114.

The display control unit 114 performs display control to cause a display unit 180 to display the generated cross section image. The user checks the cross section image displayed by the display control unit 114. Upon determining that the position of the designation point designated in the three-dimensional image data matches that on the cross section image, the user inputs an instruction to the image processing apparatus via a UI (not shown). When this instruction is input, the position of the designation point is stored in a storage unit (not shown) in the image processing apparatus 100, and the designation point designation processing is complete.

The overall processing procedure performed by the image processing apparatus 100 is the same as that in the flowchart shown in FIG. 3 except for the contents of processing in each step. The contents of processing will be specifically described below.

(Obtaining of Data)

In step S300, the obtaining unit 102 obtains the first three-dimensional image data (an MRI image of the breast in a prone position) and the three-dimensional coordinate values of a feature point group.

(Designation of Designation Point)

In step S301, the designation unit 106 performs the processing of determining the position of the first feature point in the first three-dimensional image data.

(Selection of Feature Points)

In step S302, the selection unit 108 selects a feature point (feature point A) nearest to the designation point and a feature point (feature point B) second nearest to the designation point from a feature point group in the first three-dimensional image data. Note that the method of selecting feature points is not limited to this, and it is possible to use various methods as in the first selection described in step S302 in the first embodiment.

(Calculation of Cut Plane)

In step S303, the calculation unit 110 determines or changes a cut plane. If the process shifts from step S302 or S309 to step S303, the calculation unit 110 determines the cut plane determined based on the designation point designated by the designation unit 106 and the two feature points selected by the selection unit 108 in the first three-dimensional imaged data.

If the process shifts from step S307 to step S303, the calculation unit 110 determines a new cut plane by applying the change parameter obtained in step S307 to the cut plane calculated by the processing previously executed in step S303.

(Generation of Cross Section Image)

In step S304, the generation unit 112 generates a cross section image of the first three-dimensional image data along the cut plane determined or changed by the calculation unit 110.

(Display of Cross Section Image)

In step S305, the display control unit 114 causes the display unit 180 to display a cross section image. The user as a person in charge of diagnosis sees the cross section image and can check whether the position of a designation point matches the position of a lesion portion. Note that the display control unit 114 can also superimpose and display various types of graphic patterns on a cross section image.

(Changing of Cut Plane)

In S306, the image processing apparatus 100 changes the cut plane of the first three-dimensional image data and determines whether the check is continued. For example, the user inputs information indicating the determination of a change by clicking the cut plane changing button (cut plane changing unit) arranged on the display unit 180 with the mouse. If the user inputs information indicating the determination of a change, the process advances to step S307. If the user inputs no information indicating the determination of a change, the process advances to step S308.

(Obtaining of Change Parameter for Cut Plane)

In step S307, the changing operation unit 104 obtains a change parameter for changing a cut plane of the first three-dimensional image data, and the process returns to step S303. As a change parameter, the rotation angle L around a straight line connecting two feature points as an axis is obtained. It is possible to obtain this parameter by operating the mouse of the changing operation unit 104. For example, the changing operation unit 104 obtains the rotation angle L based on the changing operation of the changing operation unit 104 (for example, the position, movement amount, moving direction, and the like of the mouse during the pressing of a button of the mouse). The details of the operation of obtaining the rotation angle L are the same as those described in the first embodiment.

(Determination on Whether Designation Point is Re-designated)

In step S308, the image processing apparatus 100 determines whether a designation point in the first three-dimensional image data is re-designated. If the user, who has seen the cross section image displayed in step S305, determines that a designation point does not correspond to that in the cross section image, he/she inputs information indicating the re-designation of a designation point. If the user inputs information indicating the determination of re-designation, the process advances to step S309. If the user inputs no information indicating the determination of re-designation, the process advances to step S310.

(Re-designation of Designation Point)

In step S309, when an instruction to re-designate a designation point is issued, the designation unit 106 of the image processing apparatus 100 designates a designation point different from the designation point designated in step S301 in the three-dimensional image data. The designation unit 106 re-designates the position of a designation point in the first or second three-dimensional image data to the position of a different designation point. The process then returns to step S303. Each unit of the image processing apparatus 100 performs the same processing as that in step S303 and the subsequent steps. The user observes the first cross section image, and can accurately re-designate the position of a lesion portion of interest or corresponding lesion portion while multidirectionally evaluating the degree of similarity between, for example, the way how the lesion portion indicated by the designation point looks and the way how the peripheral portion indicated by feature points looks.

(Determination of End of Designation Processing)

In step S310, the image processing apparatus 100 determines whether to terminate designation processing for a designation point in the first three-dimensional image data. The user inputs information indicating the determination of termination by, for example, clicking the end button arranged on the display unit 180 with the mouse. If it is determined that the designation processing is terminated, the process advances to step S311. If it is determined that the designation processing is not terminated, the process returns to step S305. Each unit of the image processing apparatus 100 then performs processing similar to that in step S305 and the subsequent steps. In this case, if there is no input for a change of a cut plane or no input for re-designation of a designation point, the process is set in a standby state while the cross section image is displayed until an input of termination is received, and an input is accepted.

(Output of Designation Point)

In step S311, the image processing apparatus 100 stores the position of a designation point in the storage unit (not shown). In addition, the display control unit 114 outputs the information of a designation point to the display unit 180 and causes the display unit 180 to display the information.

According to this embodiment, it is possible to generate and display a cross section image including the designation point designated with respect to a lesion portion in one three-dimensional image data and the two feature points selected based on the positional relationship with the designation point. This can support diagnosis of the lesion portion.

Although each embodiment has been described in detail above, the present invention can take embodiments as a system, apparatus, method, program, storage medium, and the like. More specifically, the present invention can be applied to a system constituted by a plurality of devices by distributing the functions of an image processing apparatus, or to an apparatus including a single device.

According to the embodiments of the present invention, it is possible to generate a cross section image including a designation point indicating a portion of interest in three-dimensional image data and image features as references.

According to the embodiments of the present invention, it is possible to generate a plurality of cross section images including designation points indicating portions of interest in three-dimensional image data and sequentially selected feature points.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-163931, filed Aug. 11, 2014, and Japanese Patent Application No. 2014-163932, filed Aug. 11, 2014 which are hereby incorporated by reference herein in their entirety.

What is claimed is:

1. An image processing apparatus comprising:
an obtaining unit configured to obtain three-dimensional image data and positions of a plurality of feature points in the three-dimensional image data;
a designation unit configured to designate a designation point indicating a portion of interest in the three-dimensional image data;
a selection unit configured to select, using information determined by a position of the designation point and the positions of the plurality of feature points, a feature point from the plurality of feature points;

a generation unit configured to generate, from the three-dimensional image data, a cross section image on a plane determined based on the position of the designation point and a position of the selected feature point; and a display control unit configured to cause a display unit to display the generated cross section image.

2. The apparatus according to claim 1, wherein said selection unit selects two feature points from the plurality of feature points.

3. The apparatus according to claim 1, wherein said selection unit selects, based on distances between the designation point and the plurality of feature points, a feature point from the plurality of feature points.

4. The apparatus according to claim 3, wherein said selection unit selects a feature point positioned near the designation point.

5. The apparatus according to claim 3, wherein said selection unit selects a feature point positioned away from the designation point by not less than a predetermined distance.

6. The apparatus according to claim 1, wherein said generation unit generates, from the three-dimensional image data, a cross section image on a plane determined by the position of the designation point, a position of a reference point indicating a specific portion in the object, and the position of the feature point selected by said selection unit.

7. The apparatus according to claim 1, wherein said selection unit selects, from the plurality of feature points, a feature point so that a positional relationship between a reference point indicating a specific portion in an object, the designation point, and the feature point can satisfy a predetermined condition.

8. The apparatus according to claim 1, wherein said selection unit selects, based on comparison between a threshold and information determined using the position of the designation point and the positions of the plurality of feature points, a feature point from the plurality of feature points.

9. The apparatus according to claim 8, wherein said selection unit selects, from the plurality of feature points, two feature points so that an area of a plane formed by the designation point and the two feature points will be equal to or larger than a threshold.

10. The apparatus according to claim 8, wherein said selection unit selects, from the plurality of feature points, two feature points so that an angle formed by a line connecting the designation point and a first feature point and a line connecting the designation point and a second feature point falls within a range of a predetermined angle.

11. The apparatus according to claim 8, wherein said selection unit selects, from the plurality of feature points, a feature point so that an angle formed by a plane determined by the designation point and two feature points and a reference plane is smaller than a threshold.

12. The apparatus according to claim 1, wherein the feature point selected by said selection unit includes a reference point indicating a specific portion in an object.

13. The apparatus according to claim 1, further comprising:
a calculation unit configured to calculate, as a cut plane of the three-dimensional image data, a plane determined based on the designated designation point and the selected feature point;
wherein said generation unit generates a cross section image of the cut plane from the three-dimensional image data.

14. The apparatus according to claim 13, further comprising:
a changing operation unit configured to obtain a change parameter for changing the cut plane;
wherein said calculation unit changes the cut plane of the three-dimensional image data by changing a rotational angle based on the change parameter.

15. The apparatus according to claim 14, wherein said generation unit generates, from the three-dimensional image data, a cross section image of the cut plane calculated by said calculation unit or the cut plane changed by said calculation unit based on the change parameter.

16. The apparatus according to claim 13, wherein said designation unit re-designates, in the three-dimensional image data, a designation point different from the designation point in a case where re-designation of the designation point is instructed,
said calculation unit calculates, as a cut plane of the three-dimensional image data, a plane determined based on the re-designated designation point and the selected feature point, and
said generation unit generates a cross section image of the calculated cut plane from the three-dimensional image data.

17. The apparatus according to claim 13, wherein said selection unit re-selects a feature point different from the feature point from the plurality of feature points in a case where re-selection of the feature point is instructed,
said calculation unit calculates, as a cut plane of the three-dimensional image data, a plane determined based on the designation point and the re-selected feature point, and
said generation unit generates a cross section image of the calculated cut plane from the three-dimensional image data.

18. The apparatus according to claim 1, wherein said obtaining unit:
(a) obtains, as the three-dimensional image data, first three dimensional image data and second three dimensional image data,
(b) obtains, as the positions of the plurality of feature points, positions of a first plurality of feature points in the first three dimensional image data and positions of a second plurality of feature points in the second three dimensional image data, and
(c) obtains correspondence information that makes the positions of the first plurality of feature points and the positions of the second plurality of feature points correspond to each other,
wherein said designation unit designates a position of a first designation point in the first three-dimensional image data, and a position of a second designation point in the second three-dimensional image data,
wherein said selection unit:
(a) selects a first feature point from the first plurality of feature points using information determined by the position of the first designation point and the positions of the first plurality of feature points, and
(b) selects, based on the correspondence information, a second feature point which corresponds to the selected first feature point from the second plurality of feature points,
wherein said generation unit:
(a) generates a first cross section image of a first cut plane determined based on the position of the first designation point and the position of the first feature point, and (b) generates a second cross section image of a second cut plane determined based on the position of the second designation point and the position of the second feature point, and wherein said display control unit causes the display unit to display the first cross section image and the second cross section image.

19. The apparatus according to claim 1, wherein the selection unit is configured to select, based on a predetermined selection order, the feature point to be used to generate the cross section image of the three dimensional image data from the plurality of feature points.

20. An image processing method for an image processing apparatus, comprising:
- an obtaining step of obtaining three-dimensional image data and positions of a plurality of feature points in the three-dimensional image data;
- a designation step of designating a designation point indicating a portion of interest in the three-dimensional image data;
- a selection step of selecting, using information determined by a position of the designation point and the positions of the plurality of feature points, a feature point from the plurality of feature points;
- a generation step of generating, from the three-dimensional image data, a cross section image on a plane determined based on the position of the designation point and a position of the selected feature point; and
- a display control step of causing a display unit to display the generated cross section image.

21. The method according to claim 20, wherein the selection step selects, based on a predetermined selection order, the feature point to be used to generate the cross section image of the three-dimensional image data from the plurality of feature points.

22. A non-transitory computer-readable storage medium storing a program for causing a computer to function as each unit of an image processing apparatus comprising:
- an obtaining unit configured to obtain three-dimensional image data and positions of a plurality of feature points in the three-dimensional image data;
- a designation unit configured to designate a designation point indicating a portion of interest in the three-dimensional image data;
- a selection unit configured to select, using information determined by a position of the designation point and the positions of the plurality of feature points, a feature point from the plurality of feature points;
- a generation unit configured to generate, from the three-dimensional image data, a cross section image on a plane determined based on the position of the designation point and a position of the selected feature point; and
- a display control unit configured to cause a display unit to display the generated cross section image.

23. The non-transitory computer-readable storage medium according to claim 22, wherein the selection unit is configured to select, based on a predetermined selection order, the feature point to be used to generate the cross section image of the three dimensional image data from the plurality of feature points.

24. A medical image diagnostic system comprising:
- an imaging unit configured to image three-dimensional image data;
- an obtaining unit configured to obtain three-dimensional image data and positions of a plurality of feature points in the three-dimensional image data;
- a designation unit configured to designate a designation point indicating a portion of interest in the three-dimensional image data;
- a selection unit configured to select, using information determined by a position of the designation point and the positions of the plurality of feature points, a feature point from the plurality of feature points;
- a generation unit configured to generate, from the three-dimensional image data, a cross section image on a plane determined based on the position of the designation point and a position of the selected feature point; and
- a display control unit configured to cause a display unit to display the generated cross section image.

25. The system according to claim 24, wherein the selection unit is configured to select, based on a predetermined selection order, the feature point to be used to generate the cross section image of the three dimensional image data from the plurality of feature points.

* * * * *